United States Patent
Hegemann et al.

(10) Patent No.: US 7,849,549 B2
(45) Date of Patent: *Dec. 14, 2010

(54) ORAL BRUSHING DEVICES

(75) Inventors: Kenneth J. Hegemann, Escondido, CA (US); Rob Hegemann, Escondido, CA (US); Jay Hegemann, Escondido, CA (US); Tiana L. K. Buschmann, Escondido, CA (US)

(73) Assignee: CRA Labs, Inc., Escondido, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/170,611

(22) Filed: Jul. 10, 2008

(65) Prior Publication Data
US 2008/0276390 A1  Nov. 13, 2008

Related U.S. Application Data

(63) Continuation of application No. 11/223,365, filed on Sep. 9, 2005, now Pat. No. 7,757,328, and a continuation of application No. 10/357,564, filed on Feb. 5, 2003, now Pat. No. 7,059,853.

(60) Provisional application No. 60/609,093, filed on Sep. 9, 2004, provisional application No. 60/409,760, filed on Sep. 10, 2002, provisional application No. 60/403,915, filed on Aug. 15, 2002, provisional application No. 60/385,366, filed on Jun. 3, 2002.

(51) Int. Cl.
*A61C 17/34* (2006.01)

(52) U.S. Cl. ......................................... 15/22.2; 15/22.1

(58) Field of Classification Search ................... 15/22.1, 15/22.2, 167.1, 167.2
See application file for complete search history.

(56) References Cited

U.S. PATENT DOCUMENTS

| D48,666 S | 3/1916 | Boccia |
| D53,715 S | 8/1919 | Samson |
| 1,679,946 A | 8/1928 | Ruff |

(Continued)

FOREIGN PATENT DOCUMENTS

CH  179403 A  9/1935

(Continued)

OTHER PUBLICATIONS

Acrylonitrile butadiene styrene. Granta Material Intelligence. www.grantadesign.com/solutions/education/ABS.htm.*

(Continued)

*Primary Examiner*—Shay L Karls
(74) *Attorney, Agent, or Firm*—Peter B. Scull; Kristina M. Kalan; Berenbaum Weinshienk PC

(57) ABSTRACT

An oral hygiene device having two toothbrushes connected or connectable to the end of a handle, the one or more toothbrushes providing a desirable fit about the teeth and/or gums and/or providing a desirable brushing action. An oral hygiene device hereof may provide for mechanically providing the brushing movements of the professionally recommended manual tooth-brushing method known as the "Bass" or "Modified Bass" technique to thus reduce or eliminate the element of human error associated with the brushing of a user's teeth and gums.

15 Claims, 34 Drawing Sheets

U.S. PATENT DOCUMENTS

| | | | |
|---|---|---|---|
| 1,830,995 A | 11/1931 | Genn | |
| 1,908,509 A | 5/1933 | Davis | |
| 2,093,383 A | 9/1937 | Rudof et al. | |
| 2,528,992 A | 11/1950 | Barr | |
| 2,682,066 A | 6/1954 | Keely | |
| 2,771,624 A | 11/1956 | Ripper | |
| 2,807,820 A | 10/1957 | Dinhofer | |
| 3,178,754 A | 4/1965 | Cleverdon | |
| 3,227,158 A | 1/1966 | Mattingly | |
| 3,241,239 A | 3/1966 | Ellis | |
| 3,284,829 A | 11/1966 | Allen | |
| 3,393,673 A | 7/1968 | Mattingly | |
| 3,401,690 A | 9/1968 | Martin | |
| 3,425,410 A | 2/1969 | Cammack | |
| 3,452,746 A | 7/1969 | Shanhouse | |
| 3,453,969 A | 7/1969 | Mattingly | |
| 3,465,751 A | 9/1969 | Powers | |
| 3,467,083 A | 9/1969 | Mattingly | |
| 3,623,175 A | 11/1971 | Emerson | |
| 3,732,589 A | 5/1973 | Burki | |
| 3,742,942 A | 7/1973 | Westline | |
| 3,753,435 A | 8/1973 | Blasnik | |
| 3,878,577 A | 4/1975 | Jousson | |
| 3,925,841 A * | 12/1975 | Caliendo | 15/23 |
| 3,935,971 A | 2/1976 | Papoff | |
| 3,937,582 A | 2/1976 | Del Bon | |
| 3,953,907 A | 5/1976 | Froidevaux | |
| 3,984,890 A | 10/1976 | Collis | |
| 4,048,690 A | 9/1977 | Wolfson | |
| 4,060,870 A | 12/1977 | Cannarella | |
| 4,071,956 A | 2/1978 | Andress | |
| 4,108,167 A | 8/1978 | Hickman et al. | |
| 4,141,352 A | 2/1979 | Ebner et al. | |
| 4,146,020 A | 3/1979 | Moret et al. | |
| 4,223,417 A | 9/1980 | Solow | |
| 4,225,994 A | 10/1980 | Stoltz | |
| 4,302,186 A | 11/1981 | Cammack et al. | |
| 4,346,492 A | 8/1982 | Solow | |
| 4,498,209 A | 2/1985 | Weiss | |
| 4,498,269 A | 2/1985 | Andreasen | |
| 4,534,340 A | 8/1985 | Kerr et al. | |
| 4,630,326 A | 12/1986 | Stevens | |
| 4,766,630 A | 8/1988 | Hegemann | |
| 4,795,347 A | 1/1989 | Maurer | |
| 4,989,590 A | 2/1991 | Baum et al. | |
| D315,450 S | 3/1991 | Wagner | |
| 5,000,684 A | 3/1991 | Odrich | |
| 5,033,150 A * | 7/1991 | Gross et al. | 15/22.1 |
| 5,036,562 A | 8/1991 | Reynolds | |
| 5,062,413 A | 11/1991 | Bullard | |
| 5,068,939 A | 12/1991 | Holland | |
| 5,094,256 A | 3/1992 | Barth | |
| 5,148,567 A | 9/1992 | Daub | |
| 5,177,826 A | 1/1993 | Vrignaud et al. | |
| 5,199,604 A | 4/1993 | Palmer et al. | |
| 5,208,988 A | 5/1993 | Edelman | |
| D339,692 S | 9/1993 | Schneider | |
| 5,253,382 A | 10/1993 | Beny | |
| 5,259,083 A | 11/1993 | Stansbury, Jr. | |
| 5,273,428 A | 12/1993 | Fischer | |
| 5,305,491 A | 4/1994 | Hegemann | |
| 5,316,027 A | 5/1994 | Klinkhammer | |
| 5,327,607 A | 7/1994 | Wagner | |
| 5,342,196 A | 8/1994 | Van Hale | |
| 5,406,664 A | 4/1995 | Hukuba | |
| 5,407,254 A | 4/1995 | Hegemann | |
| 5,443,386 A | 8/1995 | Viskup | |
| 5,458,563 A | 10/1995 | Stewart | |
| 5,497,526 A | 3/1996 | Klinkhammer | |
| 5,570,709 A | 11/1996 | Haddad et al. | |
| 5,593,304 A | 1/1997 | Ram | |
| 5,669,097 A | 9/1997 | Klinkhammer | |
| 5,673,454 A | 10/1997 | Quintanilla et al. | |
| D385,702 S | 11/1997 | Okada | |
| D386,315 S | 11/1997 | Vrignaud | |
| 5,733,117 A | 3/1998 | Coss et al. | |
| 5,758,380 A | 6/1998 | Vrignaud | |
| 5,800,367 A | 9/1998 | Saxer et al. | |
| RE35,941 E | 11/1998 | Stansbury, Jr. | |
| D401,414 S | 11/1998 | Vrignaud | |
| D401,415 S | 11/1998 | Vrignaud | |
| D401,416 S | 11/1998 | Vrignaud | |
| D401,417 S | 11/1998 | Vrignaud | |
| D401,418 S | 11/1998 | Vrignaud | |
| 5,853,290 A | 12/1998 | Winston | |
| 5,934,762 A | 8/1999 | Vrignaud | |
| 5,947,729 A | 9/1999 | Bell | |
| 6,019,905 A | 2/2000 | Waggoner | |
| 6,138,310 A * | 10/2000 | Porper et al. | 15/22.2 |
| 6,152,733 A | 11/2000 | Hegemann et al. | |
| 6,203,320 B1 | 3/2001 | Williams et al. | |
| 6,233,773 B1 | 5/2001 | Karge et al. | |
| 6,401,288 B1 * | 6/2002 | Porper et al. | 15/22.1 |
| 6,920,660 B2 * | 7/2005 | Lam | 15/22.1 |
| 7,059,853 B2 | 6/2006 | Hegemann | |
| 2003/0013063 A1 | 1/2003 | Goldman | |

FOREIGN PATENT DOCUMENTS

| | | | |
|---|---|---|---|
| DE | 2735427 A1 | 2/1979 | |
| DE | 4115943 A1 | 11/1991 | |
| EP | 0611533 A1 | 8/1994 | |
| EP | 865770 A1 | 9/1998 | |
| FR | 588348 A | 5/1925 | |
| FR | 855253 A | 5/1940 | |
| FR | 881678 A | 5/1943 | |
| FR | 911243 A | 7/1946 | |
| FR | 2618651 A1 | 2/1989 | |
| FR | 2641680 A1 | 7/1990 | |
| GB | 2192784 A | 1/1988 | |
| WO | 8000909 A1 | 5/1980 | |
| WO | 8901303 A1 | 2/1989 | |

OTHER PUBLICATIONS

Office Action for U.S. Appl. No. 10/357,564, U.S. Patent and Trademark Office, mailed Oct. 29, 2004.

Response to Office Action for U.S. Appl. No. 10/357,564, submitted to the U.S. Patent and Trademark Office on Nov. 29, 2004.

Office Action for U.S. Appl. No. 10/357,564, U.S. Patent and Trademark Office, mailed on Feb. 17, 2005.

Response to Office Action for U.S. Appl. No. 10/357,564, submitted to the U.S. Patent and Trademark Office on May 17, 2005.

Office Action for U.S. Appl. No. 10/357,564, U.S. Patent and Trademark Office, mailed Aug. 23, 2005.

Response to Office Action for U.S. Appl. No. 10/357,564, submitted to the U.S. Patent and Trademark Office on Nov. 22, 2005.

Notice of Allowance for U.S. Appl. No. 10/357,564, U.S. Patent and Trademark Office, mailed on Feb. 23, 2006.

Peristaltic Pump, http://wikipedia.org/wiki/Peristaltic_pump, Sep. 2008.

Office Action for U.S. Appl. No. 11/453,307, U.S. Patent and Trademark Office, mailed on Jan. 7, 2008.

Response to Office Action for U.S. Appl. No. 11/453,307, submitted to the U.S. Patent and Trademark Office on Apr. 7, 2008.

Office Action for U.S. Appl. No. 11/453,307, U.S. Patent and Trademark office, mailed Sep. 30, 2008.

Response to Office Action for U.S. Appl. No. 11/453,307, submitted to the U.S. Patent and Trademark Office on Dec. 1, 2008.

Office Action for U.S. Appl. No. 11/453,307, U.S. Patent and Trademark office, mailed on Dec. 15, 2008.

Response to Office Action for U.S. Appl. No. 11/453,307, submitted to the U.S. Patent and Trademark Office on Dec. 29, 2008.

Office Action for U.S. Appl. No. 11/453,307, U.S. Patent and Trademark office, mailed Mar. 30, 2009.

Response to Office Action for U.S. Appl. No. 11/453,307, submitted to the U.S. Patent and Trademark Office on Jun. 30, 2009.

Office Action for U.S. Appl. No. 11/453,307, U.S. Patent and Trademark office, mailed on Oct. 19, 2009.

Office Action for U.S. Appl. No. 11/864,478, U.S. Patent and Trademark office, mailed on Oct. 21, 2009.

Office Action for U.S. Appl. No. 12/168,774, U.S. Patent and Trademark office, mailed on Apr. 22, 2009.

Response to Office Action for U.S. Appl. No. 12/168,774, submitted to the U.S. Patent and Trademark Office on Jul. 22, 2009.

Office Action for U.S. Appl. No. 12/168,774, U.S. Patent and Trademark office, mailed on Oct. 20, 2009.

Office Action for U.S. Appl. No. 12/170,611, U.S. Patent and Trademark office, mailed on Apr. 24, 2009.

Response to Office Action for U.S. Appl. No. 12/170,611, submitted to the U.S. Patent and Trademark Office on Jul. 24, 2009.

Office Action for U.S. Appl. No. 29/280,205, U.S. Patent and Trademark Office, mailed Jul. 16, 2008.

Response to Office Action for U.S. Appl. No. 29/280,205, submitted to the U.S. Patent and Trademark Office on Sep. 8, 2008.

* cited by examiner

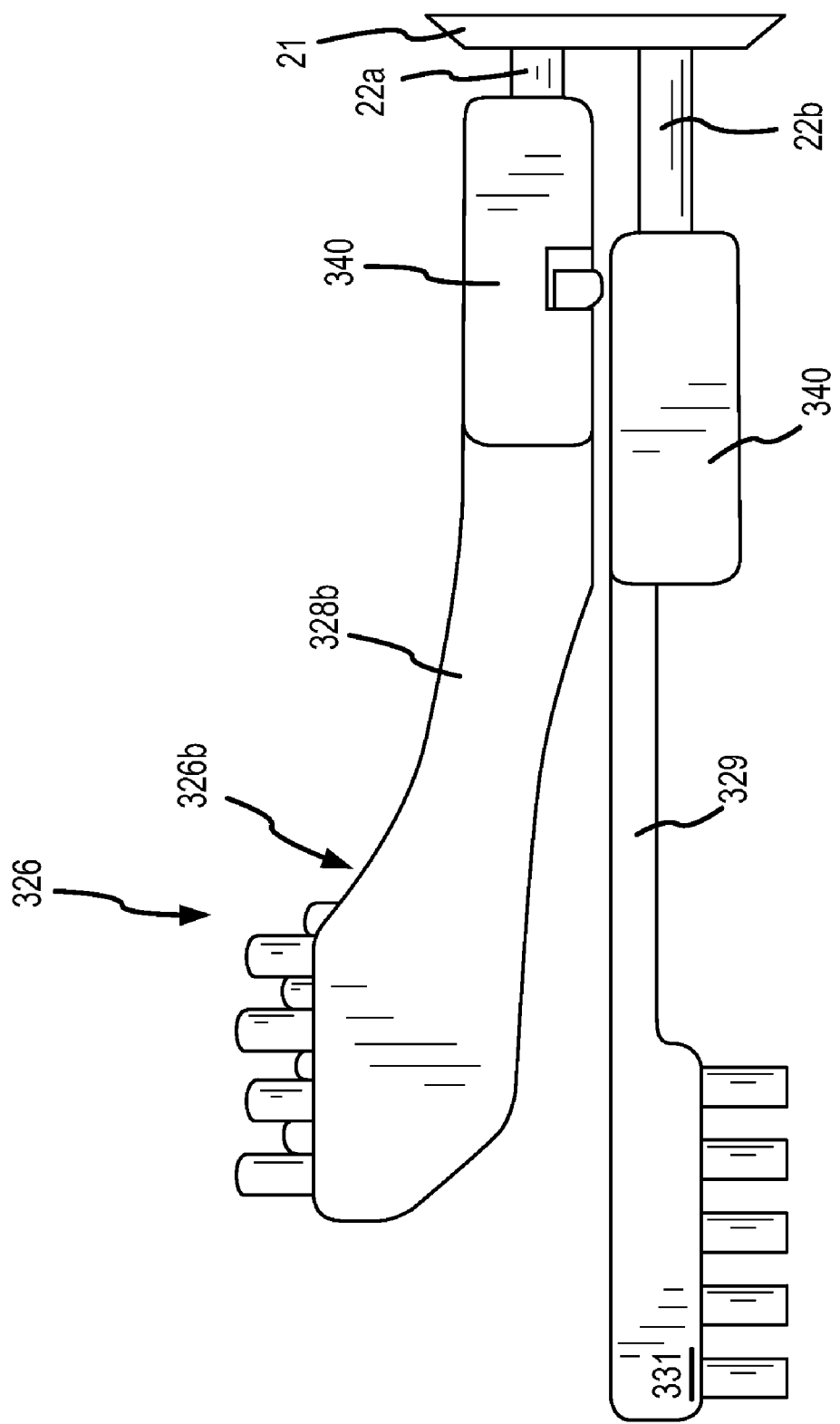

ORAL BRUSHING DEVICES

CROSS REFERENCE TO RELATED APPLICATIONS

This application is a continuation of prior U.S. application Ser. No. 11/223,365, filed Sep. 9, 2005, which claimed the benefit of U.S. Provisional Application No. 60/609,093, filed Sep. 9, 2004, and which is a continuation of prior U.S. application Ser. No. 10/357,564, filed Feb. 5, 2003, which claimed the benefit of U.S. Provisional Application Nos. 60/385,366, filed Jun. 3, 2002; 60/403,915 filed Aug. 15, 2002 and 60/409,760 filed Sep. 10, 2002.

BACKGROUND

The present development relates generally to oral cleansing devices and more particularly to power driven tooth and/or gum brushing devices, and also relates, in many implementations, to a system for using or moving one or more cleaning or brushing heads during a cleaning procedure. This may commonly include providing reciprocal cleaning head movement. Particularly useful herewith may be one or more toothbrush or like arrangements which may assist in orienting and guiding the cleansing heads within the user's mouth to provide proper cleansing and stimulation to thereby produce healthy teeth and gums.

A large proportion of the adult population suffers from some form of gum disease which in turn can and often does lead to tooth loss. An important cause of gum disease is inadequate tooth and gum brushing and gum massage. In response, a diverse array of manual and automated tooth and gum cleansing devices have been developed including electric toothbrushes, oral irrigators and automated flossers. These have been generally directed at the important basic need to clean the teeth, gums and certain parts or the whole of the mouth area. Nonetheless, many deficiencies remain with various of these devices, and for many people and in many situations, they are inadequate or unsuitable. Manual brushes, for instance, require the user to have a minimum, moderate degree of manual dexterity, particularly in attempting to achieve proper bushing technique, as for example that taught by Dr. Bass (see further description hereof below). This includes a requisite ability to firmly grasp and maneuver the brush appropriately against the dental surfaces. The tiresomeness, repetitiveness, difficulty of and/or the relative disinterestedness of many people with manual brushing leads many to do less than is necessary, often also using inappropriate brushing methods. And thus, some tooth and gum surfaces may receive inadequate brushing or may be missed altogether.

Furthermore, conventional electric or "power" toothbrushes, while often requiring less physical effort on the part of the user, still generally require human skill and dexterity, i.e., accurate human manipulation in order to achieve effective disease preventing results. Such brushes do not typically provide for achieving the Bass techniques (see further description hereof below). And, these power brushes are often more complicated than manual brushes and are more expensive and require more time in maintenance. Moreover, brushing too vigorously with electric brushes can irritate the gums or cause them to bleed excessively, possibly injuring the gums or eventually contributing to or causing them to recede.

Thus, present means of tooth and gum brushing or cleaning may be inadequate for many or even most users. Many prior means and methods are not readily capable of effective operation (see e.g., the Bass technique described below); hygienic, comfortable, and/or error-free use; simple and inexpensive maintenance; with a cost-effective purchase price, for most people in most situations. Thus, there is a need for an improved cleaning device to fill one or more of these needs.

The present disclosure is presented as a remedy for one or more of the above-mentioned drawbacks of past devices and/or methods with the provision of a dental care device which offers effective means of dental care for people of all ages, including those with natural teeth or implants, crowns, braces and bridgework, as well as for people of limited dexterity, or having other handicaps.

SUMMARY

The present disclosure provides a dental cleaning appliance and/or method for cleaning teeth and/or gums, such an appliance typically having one or more cleaning heads which are insertable into the user's mouth for the cleaning operation, the cleaning head or heads being attached to a power handle which activates movement of the cleaning head or heads which each may include one or more brushing heads and one or more brushing arms, the one or more brushing heads being reciprocable in many implementations, and also typically being disposed so as to include in further implementations a set of first brushes and a set of second brushes, each of these sets of brushes often being reciprocable in alternating opposing dispositions relative to each other. Such brush heads may also be used to definitively establish the position of the brushes in the user's mouth and maintain this position so that the bristles may effectively work on the tooth and gum surfaces and/or at the gum line (and/or elsewhere, as may be desired) as may be most appropriate for cleaning and improving oral health. The alternating reciprocation may provide a force balance such that the handle is static while the brush heads are dynamically cleaning. Note, the first and second sets of brushes may be related as top and bottom or side-to-side or otherwise as may be useful in oral care.

Accordingly, an aspect of the present disclosure is to provide an oral cleaning device including one or more brushes or other cleaning devices which may be positioned by a cleansing head in a substantially pre-selected position for cleaning and massaging of the user's teeth and gums. Another aspect of the present disclosure may be to provide an oral cleaning device including one or more brushes which are disposed in, on or adjacent a brush head assembly such that the bristles may be accurately positioned by or with assistance of the brush head assembly in a pre-selected disposition to provide for accurate brushing, cleaning and massaging of the user's teeth and gums. And yet another aspect of the present disclosure may be to provide a device in which one or more brushes may be moved such that the brushes selectively move with the cleansing head to activate the tooth and gum cleansing process with a moving bristle pattern (direction and angle) meeting the needs of a user while substantially eliminating human error.

A further aspect may be in providing an oral hygiene device which provides for mechanically mimicking or simulating the brushing movements of the most widely professionally recommended manual tooth-brushing method known as the "Bass" or "Modified Bass" technique, to thus reduce or eliminate an element of human error associated with brushing of a user's teeth and gums. The Bass method (as developed and taught by Dr. Charles Bass; see the text: Dr. Charles Bass and the Bass Method, One Man's Crusade to End Tooth Decay and Gum Disease, by Dr. Wayne Lott with Steve Brawner, Xlibris Corp., copyright 2004, particularly, pps. 97-99) is relatively famous, being recognized by the American Dental Association (the ADA), and is taught in dental schools. The Bass method (using a manual brush) is intended to properly and thoroughly clean and care for teeth and gums. The Bass instructions call for short back and forth brush movements. A difficulty with this is that many people find this problematic to do well, or perhaps they do not understand the importance or definition of "short" (often on the order of about or less than about 0.25 inches; the ADA teaches short as "tooth-wide"), or do not have patience, and soon convert to long sweeping strokes that they believe gets the job done faster (actually, sweeping long strokes can cause trenching of both teeth and gums). The present apparatuses and methods; however, provide mechanical application of the Bass Toothbrushing Method. These may rather, in many implementations, substantially automatically position the bristles at about a 45 degree angle of approach (as taught by Dr. Bass and the ADA) with application of an appropriate or correct amount of pressure to the bristles. These may then also, in many implementations, substantially automatically deliver the short back and forth brushing movements that appropriately clean the tooth and gum areas and make trenching substantially not possible. The devices and methods hereof may also substantially automatically deliver the correct movement speed that may provide for the bristles to move into the hard to reach crevices and spaces between teeth. Moreover, with the multiple brushes in many implementations hereof, these brushes "saddle" the teeth, so that it is actually the teeth that position the brush, not the user, a big factor regarding human error. Note, these features may be provided in addition to a static handle force balanced by a dynamic alternate reciprocation of the brush heads.

These and still further aspects as shall hereinafter appear are readily fulfilled by the present apparatuses and methods in a remarkably unexpected manner as will be readily discerned from the following detailed description of exemplary implementations hereof especially when read in conjunction with the accompanying drawings in which like parts bear like numerals throughout the several views.

DETAILED DESCRIPTION

The present disclosure relates in various implementations to the provision of a new and useful, substantially automated oral cleaning device and/or method including unique coactive assemblages of distinct sub-assemblies which will be described herein in some detail. More particularly, the present disclosure is directed to a plurality of elements which when considered as one or more ensembles, may provide comprehensive attainment and/or maintenance of oral cleanliness. In many implementations, achievement of the Bass and/or ADA methods of brushing may be achieved. Of these, there are several features; among which are a variety of brush heads and brush head arrangements, as well as or alternatively including dynamic brush heads with a static handle, provided by a force balance of alternating reciprocation of the brushes.

Figure 1:
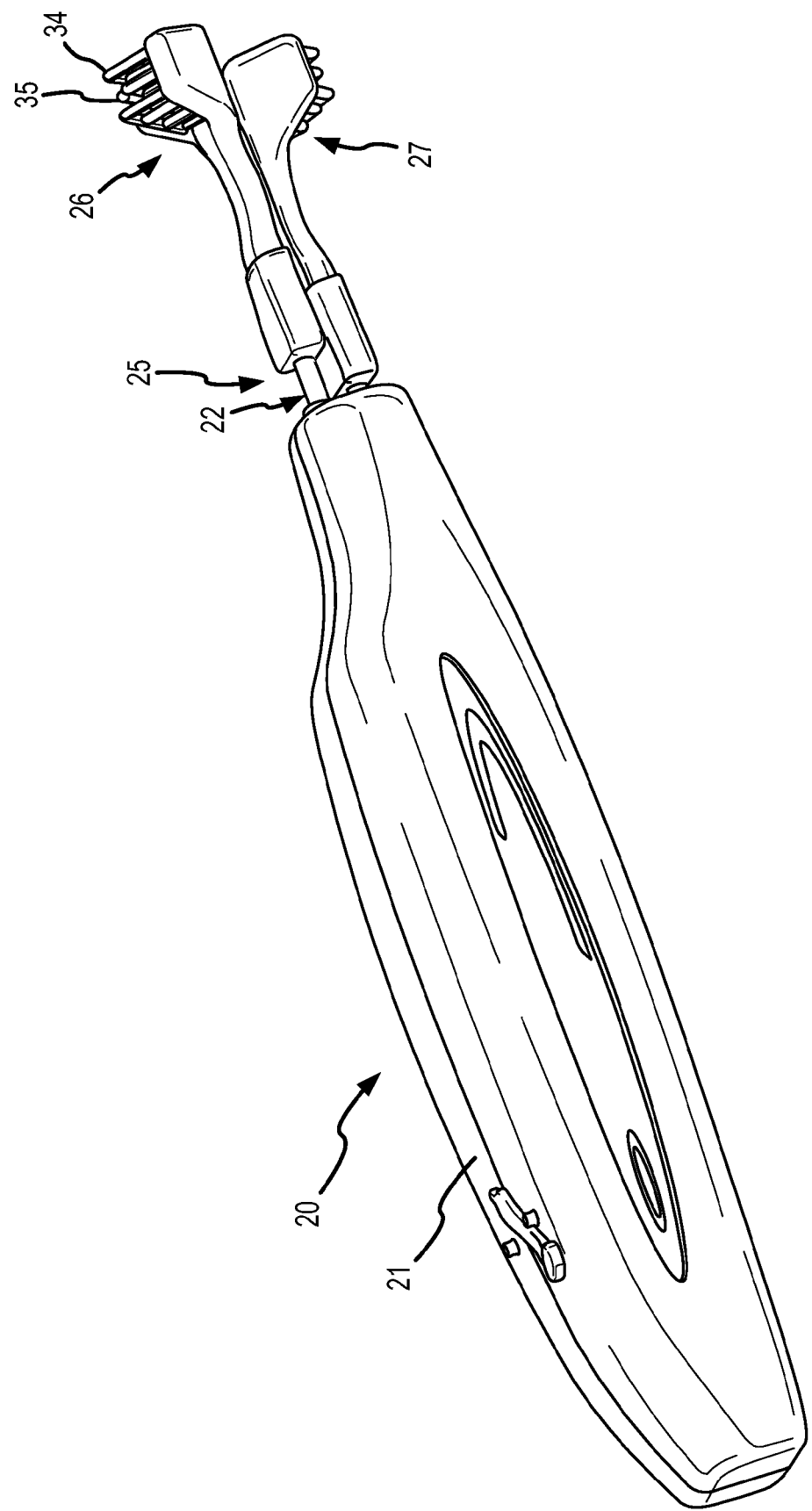
FIG. 1, is an isometric view of an oral cleaning device as described herein.
Figure 2:
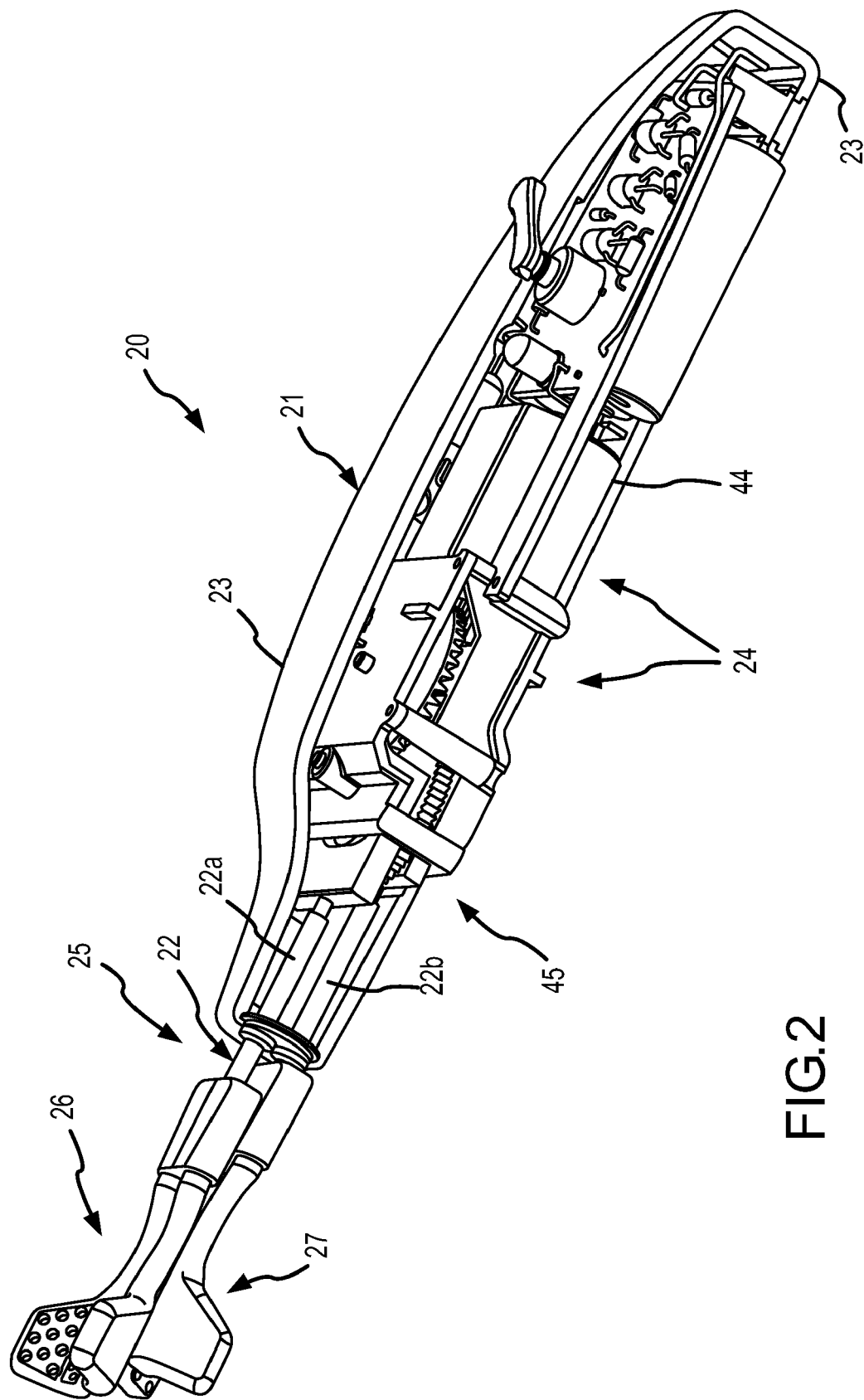
FIG. 2 is an isometric view of a cut-away portion of an oral cleaning device as described herein.

Now in more detail, though first in a relative macroscopic view; as shown at least initially in FIGS. 1 and 2, an exemplary automated tooth and/or gum cleaning device 20 hereof may generally include a control handle or module 21 (FIGS. 1 and 2) and one or more cleaning head arrangement(s), herein generally referred to as respective cleaning or brush head assemblies 26 and/or 27 (FIGS. 1 and 2). These respective cleaning or brush head assemblies 26 and/or 27 are shown positioning respective brushes, e.g. brushes 26a, 26b (see FIG. 3, et al., described below) and the brush bristles 34, 35 (again, see FIG. 3, et al., below) thereof in operative dispositions, typically in a multiple directional fashion as described further below. The control handle 21 may then also include one or more control assemblies 24 (see FIG. 2) within its structural housing 23 to provide for either securely holding the brushes or for moving or driving a brush action to and/or through the brush head assemblies 26, 27 for cleaning and massaging of the user's teeth and gums. In use, the toothbrush assemblages 26, 27 hereof may provide a totality of brushing, cleaning and massaging of the user's teeth and gums.

A handle 21 may then also include a connection configuration 25 which provides for connection of the one or more brush assemblies 26, 27 to the control handle 21. This connection may generally involve a shaft or shafts 22, two shafts being shown here, namely, shaft 22a in the relative first position, and shaft 22b in the relative second position (see FIGS. 1 and 2, inter alia), these shafts 22 stemming or emerging from the housing structure 23 of the handle 21, and then connecting or being adapted to connect to the brush assemblies 26, 27. Note, the relative first and second positions may be either top and bottom or side by side or any other orally useful position. Further details of brush mounting to/on a handle support assembly are shown and described below in particular relation to FIG. 6 (infra). Also as described in further detail below, the brushes may be made to be replaceable or interchangeable when and/or if desired and thus removably mountable on respective shaft(s) 22.

The action of the brushes or brush assemblies 26, 27 may be manually maneuvered or activated, or may more often and/or more generally be driven by a control assembly or assemblies 24, as by a motor (see motor 44 in FIG. 2 and below) and/or a mechanical system (see system 45, FIG. 2 and described further below). And, either of these actions may be delivered with either a relatively fixed disposition of the brush arms and/or brush heads relative to each other, or as is further described herein for the primary implementations hereof, where as shown e.g., in FIG. 3, the brush arms and/or heads may be reciprocated in and out alternately and/or in opposition to each other (see FIG. 4B, inter alia) More particularly, as shown, the brush assemblies 26, 27 may be disposed so that one is adapted to move inward relative to the mouth while the other is adapted to move outwardly. This is shown in FIG. 4b, e.g., wherein, the brush 26 moves or is moving inwardly relative to the mouth (outward from the handle 21), see direction arrow 53, while the brush 27 moves outward relative to the mouth (inward toward the handle 21), see direction arrow 54. Then, in an opposite reciprocal movement, not directly shown, the brush 26 moves outward mouthwise direction, while the brush 27 moves inwardly, in the opposing direction. Thus, the brush heads may then reach the teeth and gums in a desirable fashion as shown in and described relative to FIGS. 4A, 4B and 4C, below) to thereby brush away plaque and/or debris lodged in and/or between the teeth, and/or provide a vital massage of the gums, particularly adjacent the teeth. And as is further shown and described hereinbelow (see FIG. 7), a motor 44 as described herein may be activated to provide movement to a mechanical system 45 which in turn provides movement, via the shafts 22, to the brush assemblies 26, 27. As mentioned above and as will be shown and described further below, the provision of reciprocatable linear movement into and out of the oral cavity proficiently cleans the teeth and/or gums and also provides for reaching the rear most teeth as well as all of those in between.

As initially shown in FIG. 1, but, also in more detail in FIG. 3 (cumulatively including each of FIGS. 3A, 3B, 3C, 3D and 3E), each device 20 may include one or more brush or other cleaning head assemblies, here shown as brush assemblies 26, 27, which each may include one or more brushes, here see the brushes 26a, 26b of a brush assembly 26 in FIG. 3, each such brush 26a, 26b having respective brush arms 28a, 28b and brush heads 30a, 30b. The brush heads, e.g., heads 30a, 30b, may then be disposed such that adjacent brushes or sets of bristles may be used simultaneously during a brushing action. Combining multiple sets of brushing actions may provide better simulation or replacement of interproximal brushing, flossing, and/or perio-picking and/or using proxy brushes.

Moreover, it may be noted that the action shown and described relative to FIG. 3 (including the sub-parts thereof) may be exemplary of attainment or simulation of either or both the Bass and ADA methods for tooth brushing technique. The brushes are shown being reciprocated substantially linearly, and may be limited in length of stroke to the taught tooth wide, or about 0.25 inches (in some implementations on the order of between about 0.18 and about 0.25 inches).

The brushes are in many implementations hereof, see e.g., brushes 26a, 26b, disposed such that the brush heads, see e.g., heads 30a, 30b, may be disposed in or have portions thereof predisposed in a preselected angular disposition to appropriately impact the teeth and gums, the intersection thereof and/or any gaps therebetween at the desired location, height, and width thereof. As such, the heads 30a, 30b may have respective head portions, namely, side portions 36a, and crown portions 36b. These brushes 26a, 26b can then contact the teeth from one or all sides of an array of teeth 50, see e.g. the outside or cheek or bucal side 51 toward the other side, e.g., the inside and/or tongue or lingual side 52 of an array of teeth 50 and/or the crown or occlusial side 550 as shown for example in FIGS. 4A, 4B and 4C.

Figure 4A:
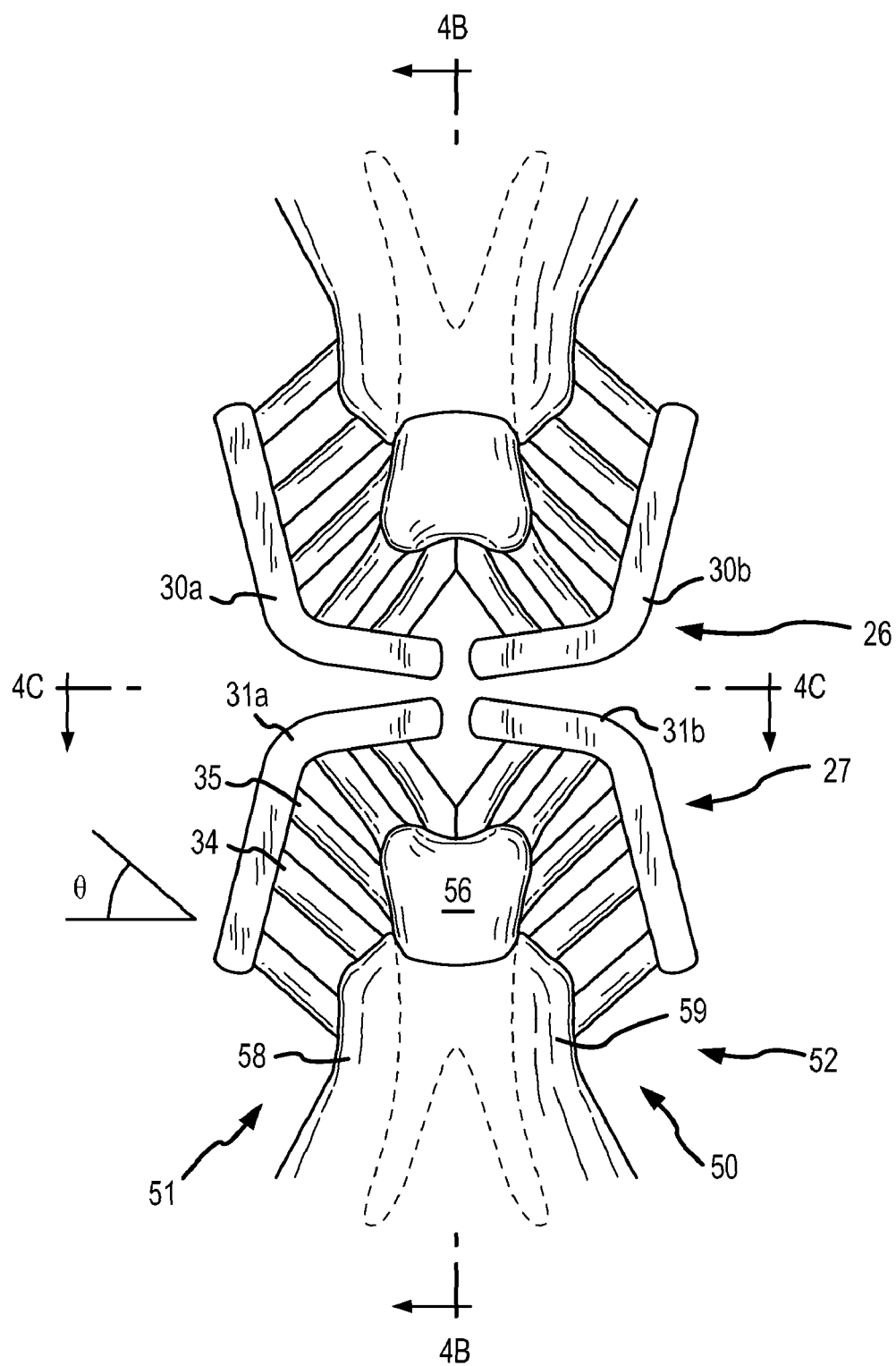
FIG. 4, which includes subpart FIGS. 4A, 4B and 4C, provides respective elevational and plan views of exemplary brushes as they may be in use according hereto.

The side portions 36a and crown portions 36b of the heads 30a, 30b may thus be disposed to have bristles 34, 35 (see below) disposed in an angular disposition, see angle θ in FIG. 4A which may thereby provide a desirable cleaning action on the respective side surfaces of the teeth with which the tips of the bristles 34, 35 may more effectively come into contact. As shown in FIG. 4A, the bristles 34, 35 are shown angled downward to provide a potentially desirable impact of the bristles 34, 35 with the gum line intersection of respective gums 58, 59 with a tooth 56. This may include an angle θ at approximately a 45 degree angle (plus or minus) for the side bristles in accordance with the American Dental Association (ADA) recommended Bass or modified Bass technique, moreover, also according to this technique, a quantity of bristles may be disposed on or impact with the teeth (as for example approximately one-half in some implementations) and another quantity of bristles on or in contact with the gums (in some cases as much as one-half the bristles). The crown bristles shown in FIGS. 3D, 3E and 4A may also be angularly disposed, though perhaps not at the approximate 45 degrees as those on the side (rather, more like a larger angle relative to the horizontal or smaller relative to the vertical orientation shown in the drawings).

It may also be desirable to provide an interaction of long bristles 34 of brushes such as brushes 26a, 26b particularly so as to substantially completely impact the deeper areas of teeth and between teeth, while having shorter bristles 35 impact the less deep, more prominent portions of teeth. For example, the long crown bristles 34 of adjacent brushes 26a, 26b may cover the interior depressed portion of the chewing or occlusial surface of the tooth, see e.g., tooth 56 in FIG. 4A, and the shorter crown bristles 35 (see FIGS. 3D and 3E) may impact the less deep extended tooth edges. Note the shorter bristles 35 may also be at a discrete angle, e.g. angle α in FIG. 3E, less pronounced than that of the longer crown bristles 34 (crown bristles 34 e.g., preferably, at something like about 5 to 20 degrees from the vertical, with the crown bristles 35 being less, from about 0 to 10). Here an angle α of about 14 or 15 degrees is shown. The shorter crown bristles 35 may thus be intended to impact and clean the higher, non-depressed, outer surfaces of the tooth. Moreover, it may be that the angle of the bristles on the crown portion 36b of the respective brush head 30a, 30b may be different, more or less than that of the side portion 36a bristles. Any combination of alternative angular dispositions may be used with the brushes of the present invention.

Figure 3A:
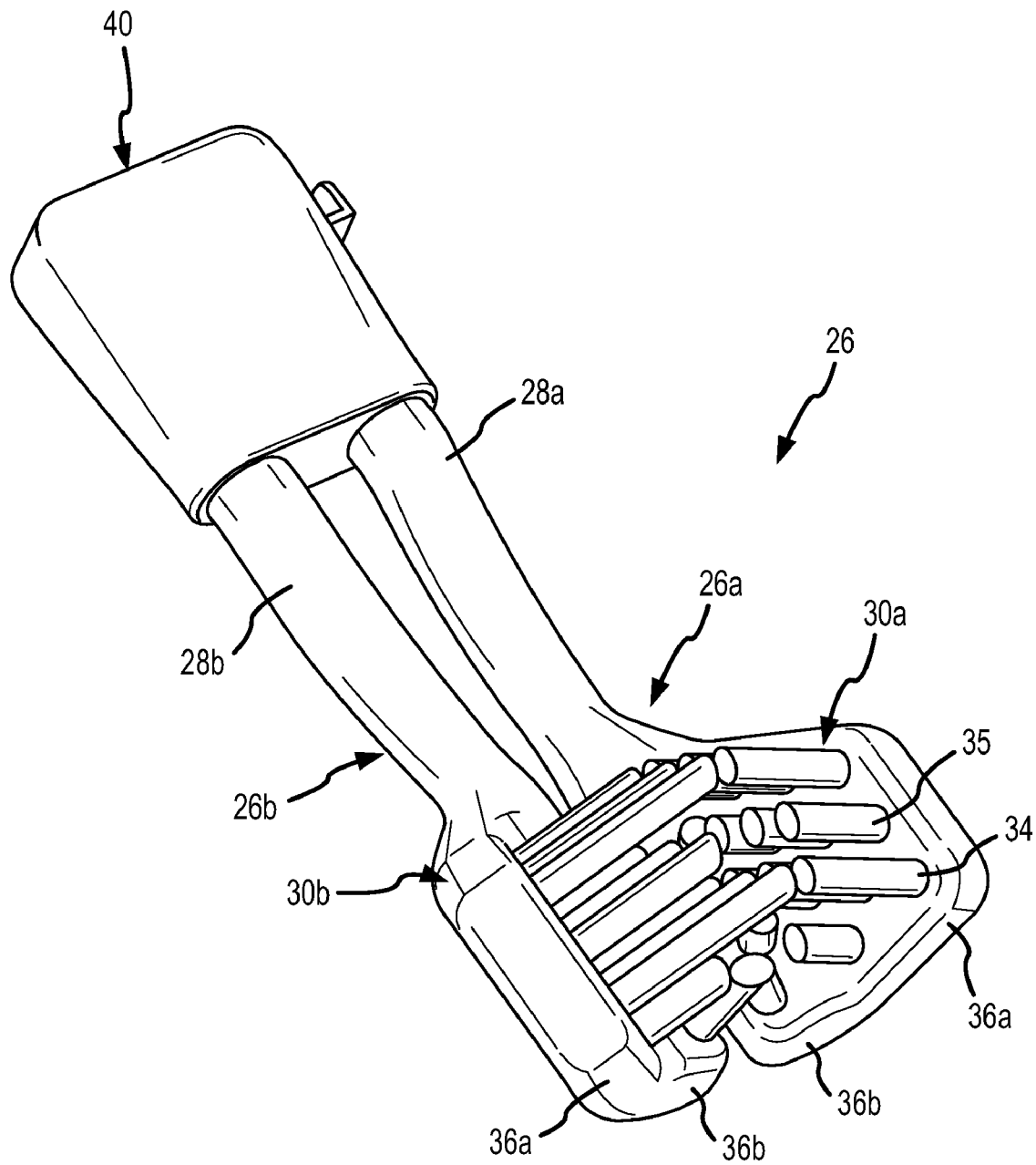
FIG. 3, which includes subpart FIGS. 3A, 3B, and 3C, 3D, and 3E, provides respective isometric and elevational views of exemplary brushes for use as part of an oral cleaning device or system as described herein.
Figure 3B:
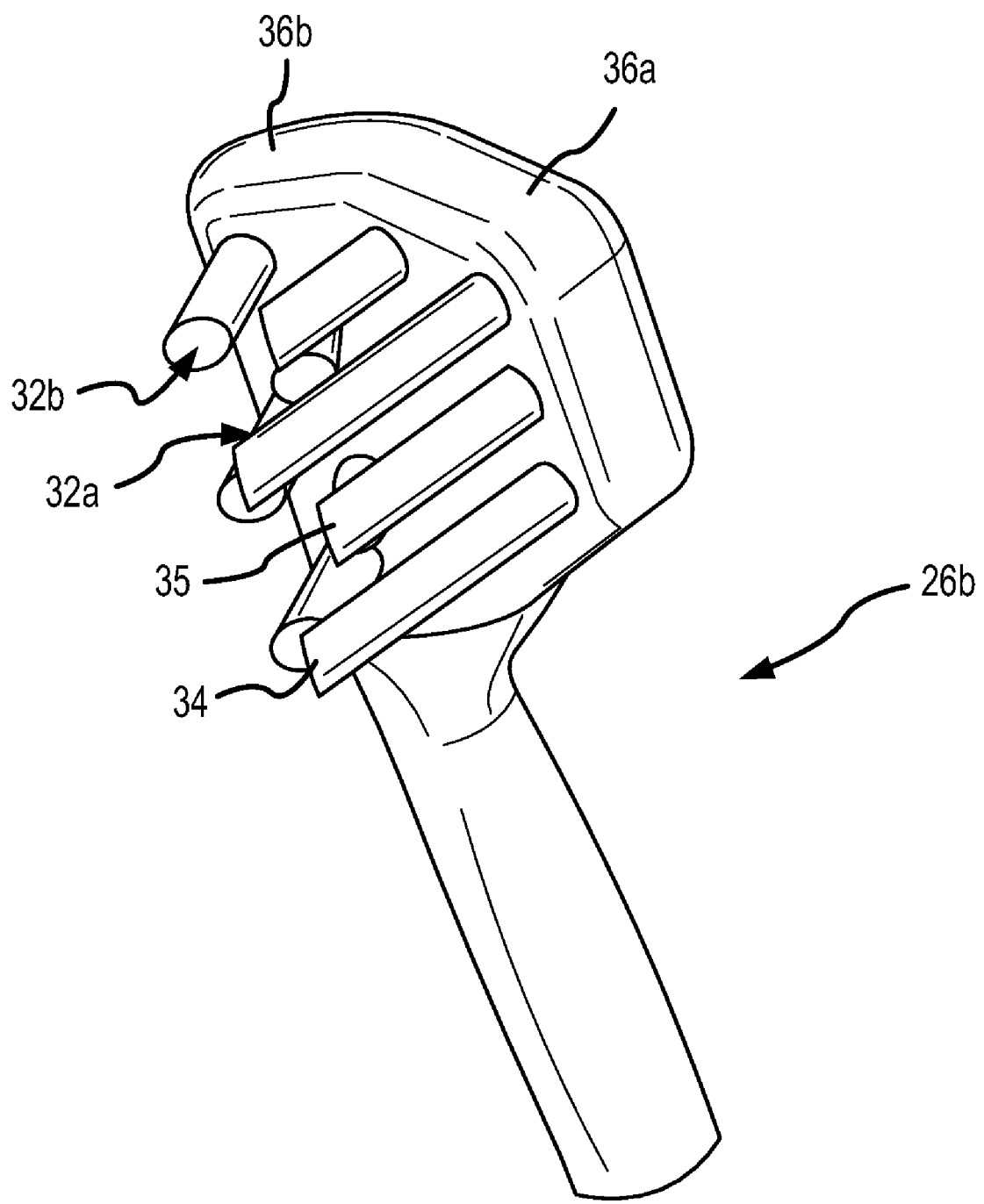
Figure 3C:
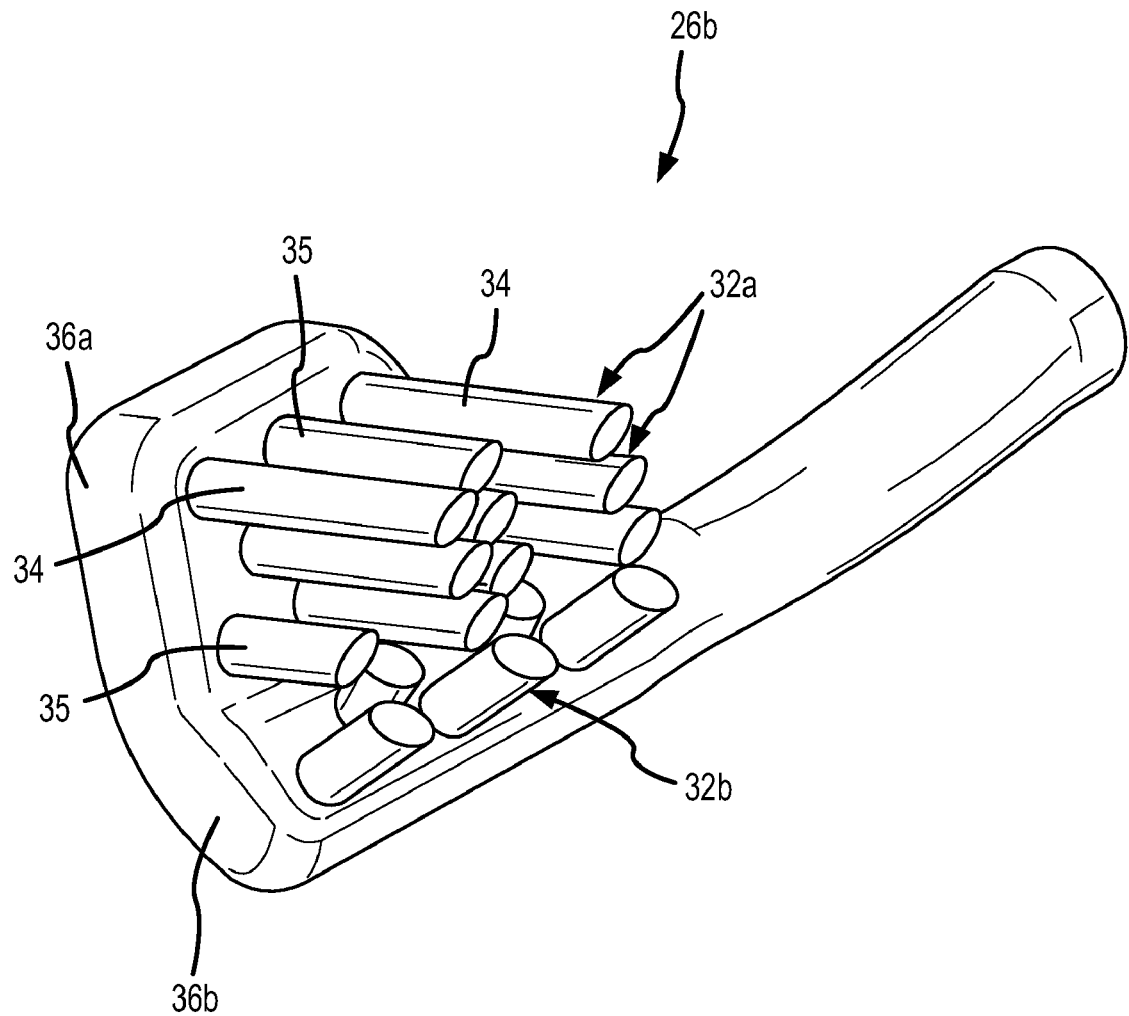
Figure 3D:
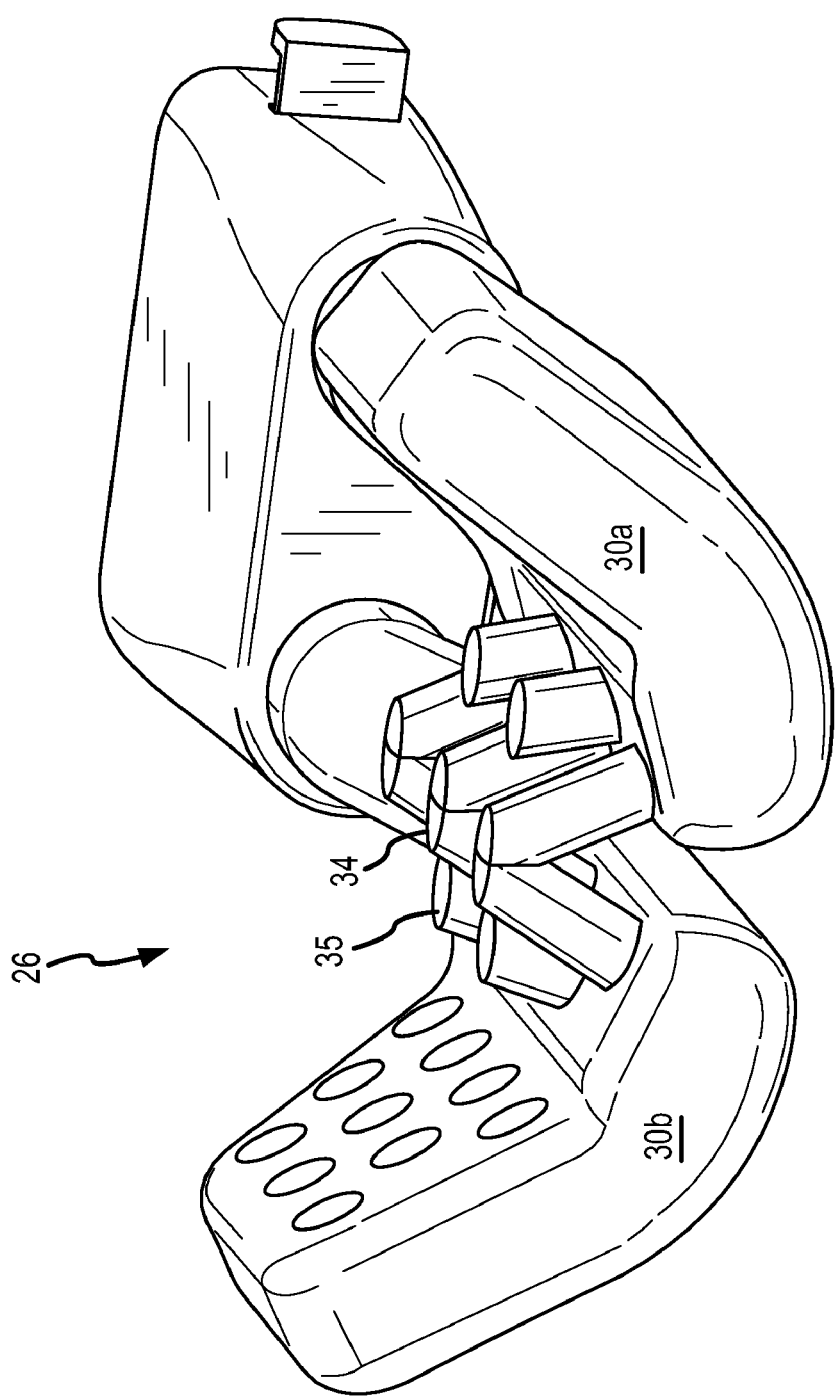
Figure 3E:
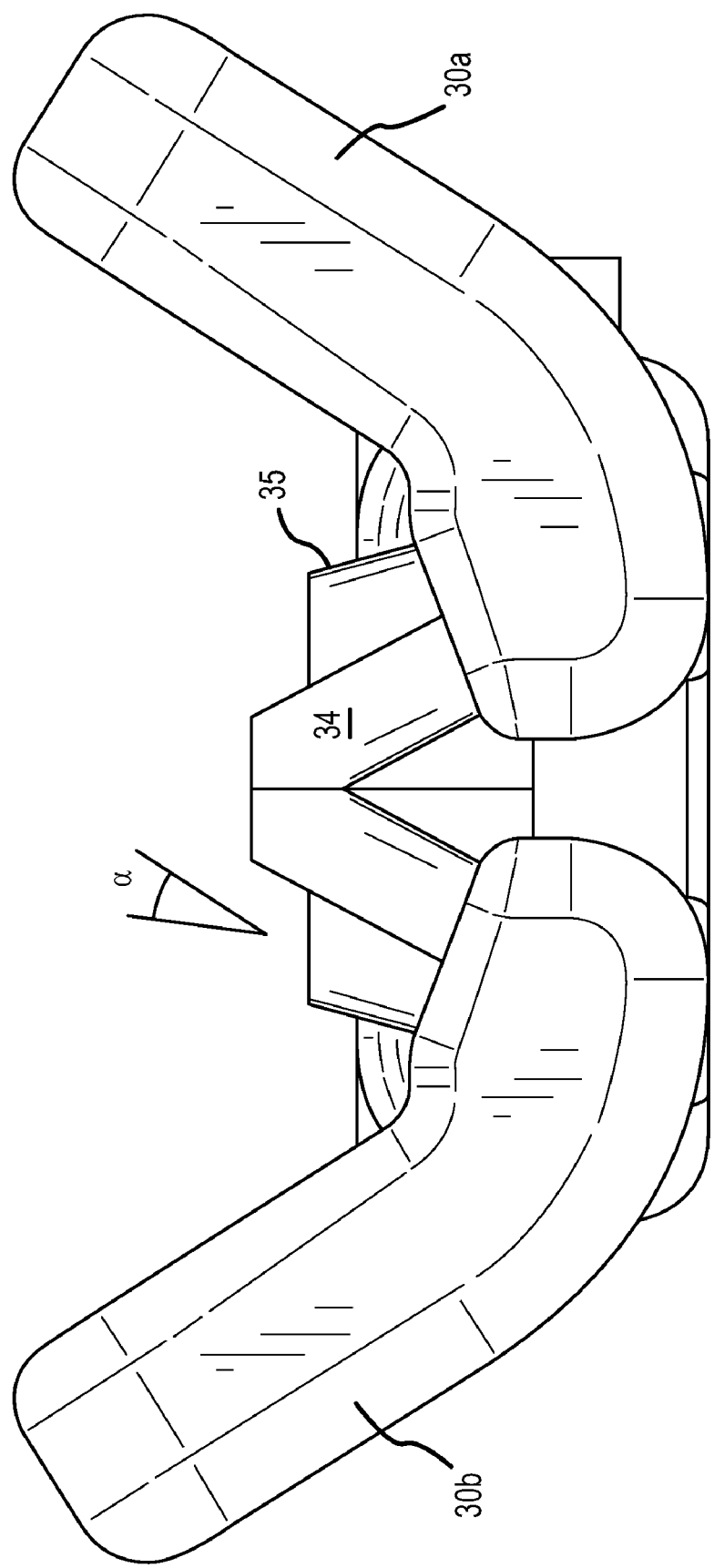
Figure 4B:
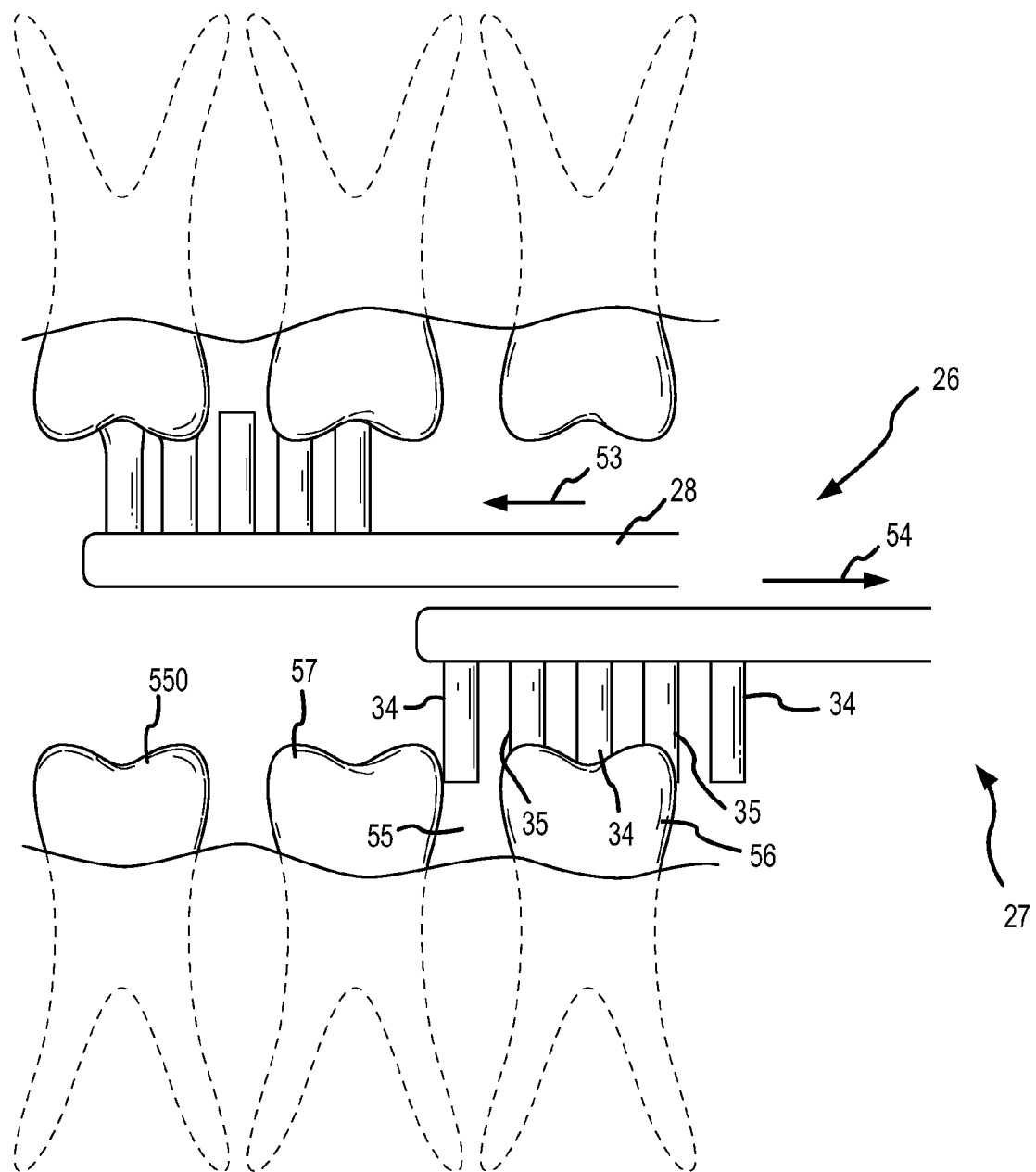
Figure 4C:
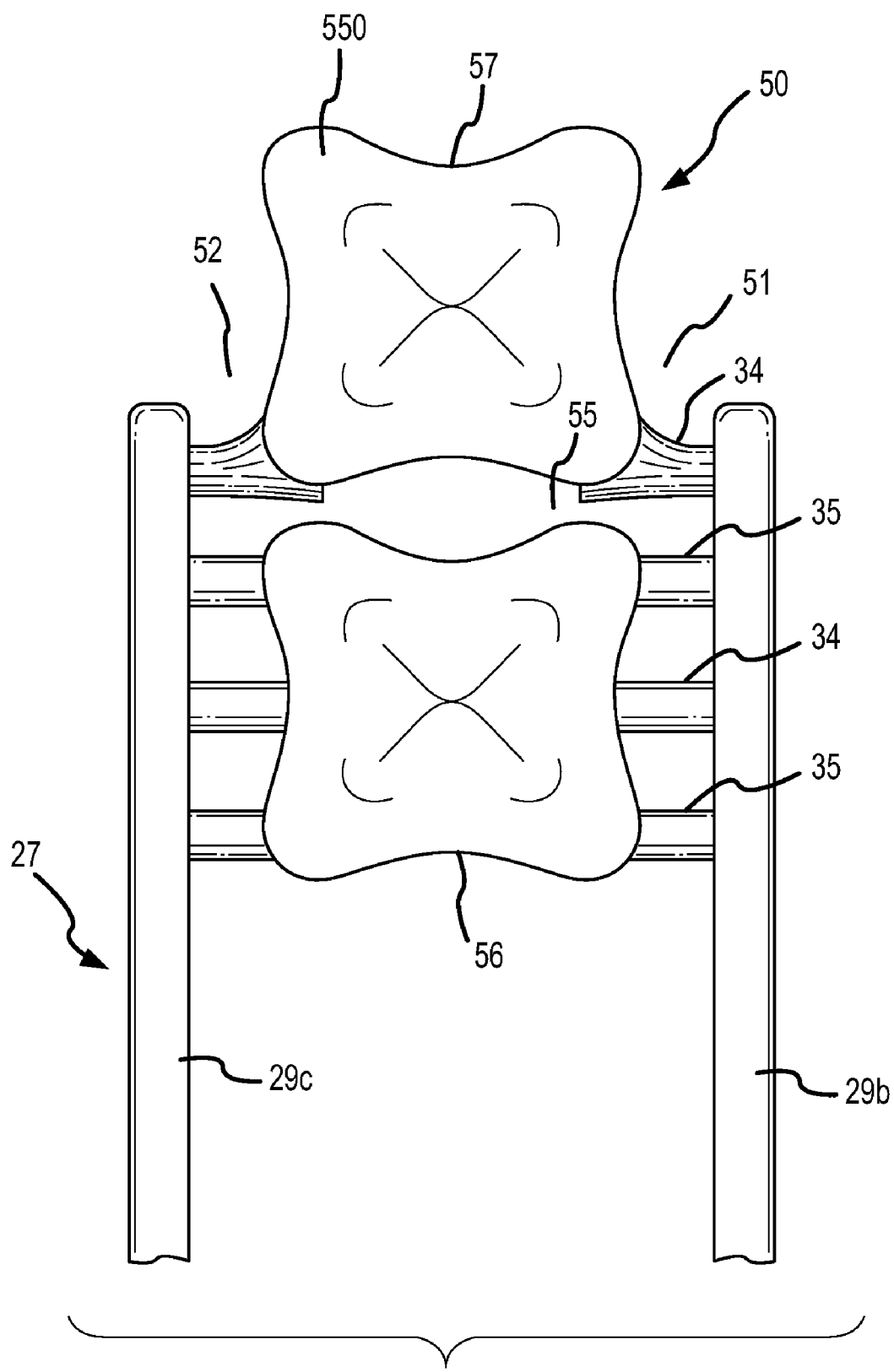

Other views of bristle dispositions are also shown, particularly of the side bristles 34, 35 in the isometric views of FIGS. 3A, 3B and 3C, as well as in the respective cross-sectional elevation and plan depictions of FIGS. 4B and 4C (as taken along respective lines 4B-4B and 4C-4C of FIG. 4A). Moreover, these uneven bristles, i.e. long bristles 34 and short bristles 35, as shown in FIGS. 3 and 4, provide bristle tip coverage of the uneven side surfaces of the tooth. For example, see the respective long and short bristles 34, 35 on the uneven side surfaces of FIG. 4A and on the uneven side surfaces of FIG. 4C. As indicated above, and as shown in FIG. 4A, these bristles may even be angled on the otherwise relatively flat crown or chewing surface of the tooth to get full coverage of the tooth surface.

In the use of angled uneven length bristles 34, 35, the bristles may first be brought into contact with the tooth, then movement of the brush and thus also of the bristles, thereby brings the different length bristles into contact with the various uneven portions of the tooth surface, at various points the long bristles are brought into contact with deeper surfaces or interproximal areas between teeth or between a tooth and gum, and the short bristles also at times being brought into contact with the less deep, more prominent surfaces, the bristle tips in both cases being brought to full, non-interfered-with usage on the respective surfaces of the teeth, the bristle tips rather than the respective sides of the bristles. The angled disposition assists by substantially simultaneously directing the bristle tips toward the surface-to-be-cleaned and resisting bending of the bristle which would lead to the bristle side coming into contact with the tooth surface rather than the bristle tip.

More particularly in a structural implementation, and, as initially shown in FIGS. 1, 3, 4 and 5, each device 20 may include one or more brush or other cleaning head assemblies, here shown as brush assemblies 26, 27, which each may include one or more brushes, here see the brushes 26a, 27a of respective brush assemblies 26, 27, each such brush 26a, 27a having respective brush arms 28, 29 and brush heads 30, 31. The brush heads, e.g., heads 30, 31, may then be disposed such that adjacent brushes or sets of bristles may be used simultaneously during a brushing action. Combining multiple sets of brushing actions may provide better simulation or replacement of interproximal brushing, flossing, and/or perio picking and/or using proxy brushes.

Also directed to a maximal bristle cleaning activity may be an option of flexible, resilient brush arms, e.g., arms 28a, 28b, 29a and/or 29b, which can contribute to the preferred maintenance of the tips of the long and short bristles 34, 35 in contact with the respective deeper and shallower tooth portions by alternately flexing outwardly during an encounter with a wider tooth or shallower oral feature and then upon encountering a deeper or narrower feature, flexing or resiling inwardly to reach inwardly toward the deeper surfaces and/or the narrower teeth. This may be a part of providing for disposing the brushes in a preselected typically optimal brushing position. And, even the trim of the bristles may contribute to this maintenance of a desired bristle angle. As such, the trim at the tips of the bristles may be angled to be parallel to the tooth surfaces (see each of the views of FIG. 3). Moreover, the short and long trim of the bristles, which as otherwise described herein is primarily directed to reaching all the uneven surfaces of the teeth, including the interproximal areas, may also contribute to maximal cleaning because if all bristles were the same length, then upon reaching a raised area, the bristles would be deflected to present the sides of the bristles against the surfaces of the teeth and the sides of the bristles are not as capable of cleaning as the tips. Thus the bristle tips, as opposed to the bristle sides, are preferred to remain on or in contact with the enamel, with the long bristles also being adapted to reach into the interproximal areas without interference or with minimal interference or obstruction of the shorter bristles by long bristle sides on enamel surface. Note, long toothbrush heads, and/or overly voluminous bristle packing on a head can also yield problems like this, where rather less bristles may be better because the interference from adjacent bristles may be minimized. Rather accurate positioning (often very or ultra accurate positioning) of bristles is favored in the present implementations as opposed to the provision of an overabundance of bristles (such as is provided in some prior art brushes in an attempt or aspiration for hopefully some or any bristle(s) to hit the mark).

Figure 5A:
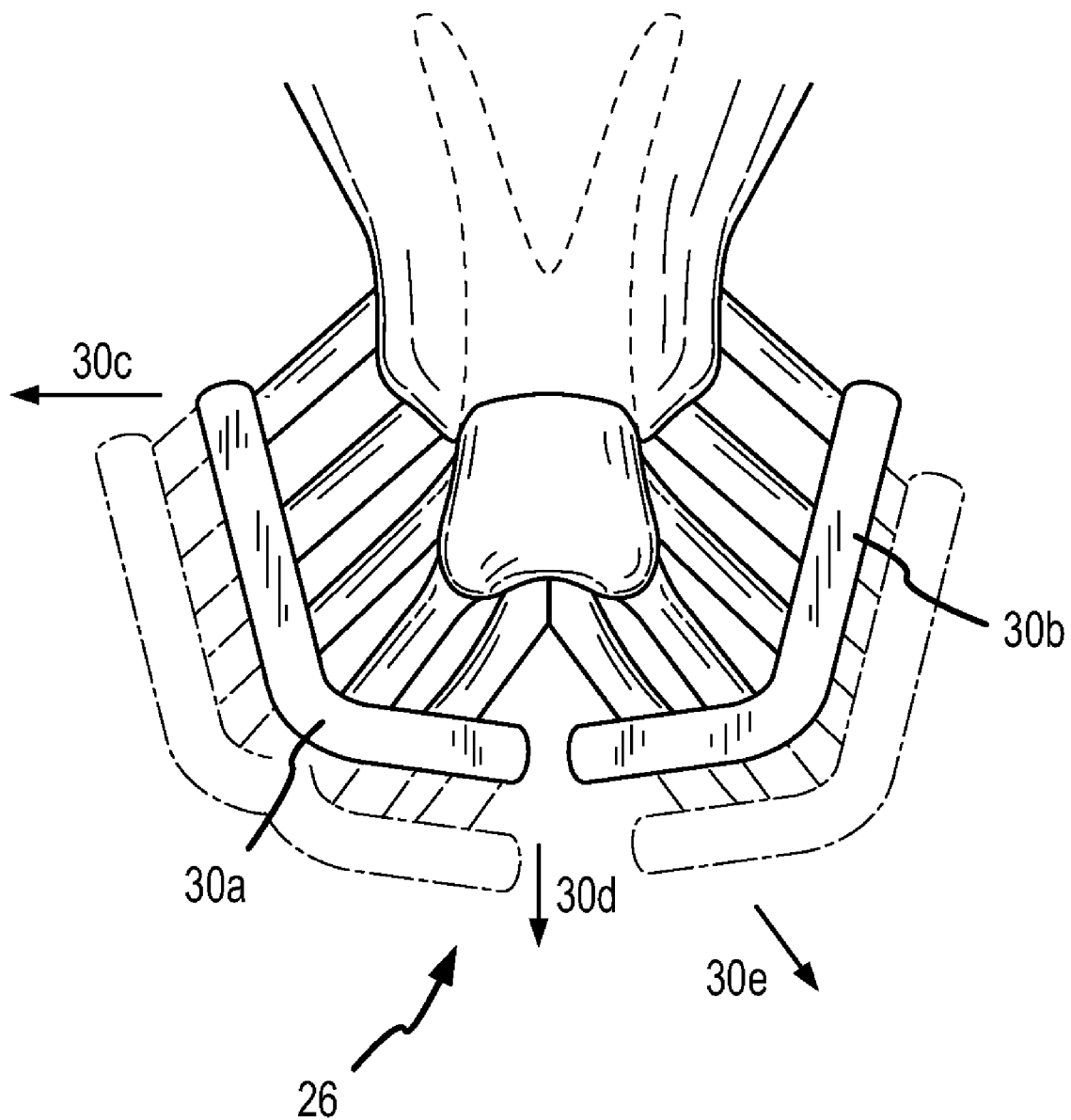
FIG. 5, which includes subpart FIGS. 5A, 5B, and 5C, provides respective elevational views of exemplary brushes for use as part of an oral cleaning device or system as described herein.

In some implementations, in order to effectively substantially eliminate human error, the present brushes may provide a relative "self-positioning" of the brush arms, brush heads and bristles relative to the teeth and gums. Self-positioning may involve disposition relative to an oral feature such as a tooth or teeth and gums, and/or may involve in and out positioning as well as swiveling heads. The in and out positioning may primarily be a result of resilient brush arms which allow for spreading of the heads away from each other when encountering a wide tooth and resiling back inwardly toward their original position when narrower surfaces are encountered. The width of the tooth can then limit the full amount of resiling, thus, the tooth determines the position; i.e., self-positioning the brushes. The heads may also have resilient characteristics, e.g. of the side relative to the crown and vice versa. The resilient arms and/or heads may thus provide for biting into the combination of brush heads, the resilience providing for applying substantially continuous force for the brush heads to continually close in on or appropriately squeeze toward the teeth large or small, spreading as necessary for the larger teeth. Note, the resiliency of the arms and/or heads may be selected so as to provide or apply a desirable, light yet operative pressure in the direction of bristles (maintaining the desirable angle, e.g. 45 degrees for the side bristles), not an overly aggressive or damaging force on the teeth and/or gums. Spreading is shown in FIG. 5A where a pair of brush heads 30a, 30b are shown as they might move outwardly (arrow 30c), downwardly (arrow 30d) or a combination of both (arrow 30e). Note also, this self-positioning particularly with resilient arms and/or heads may allow for smaller brushes to be used, where the user bites down and thereby moves the arms and gets a better fit around the tooth (a smaller brush perhaps also/alternatively being desirable due to the reduction of bristle volume and thus reduced bristle interference to maximize bristle tip effectiveness).

Figure 5B:
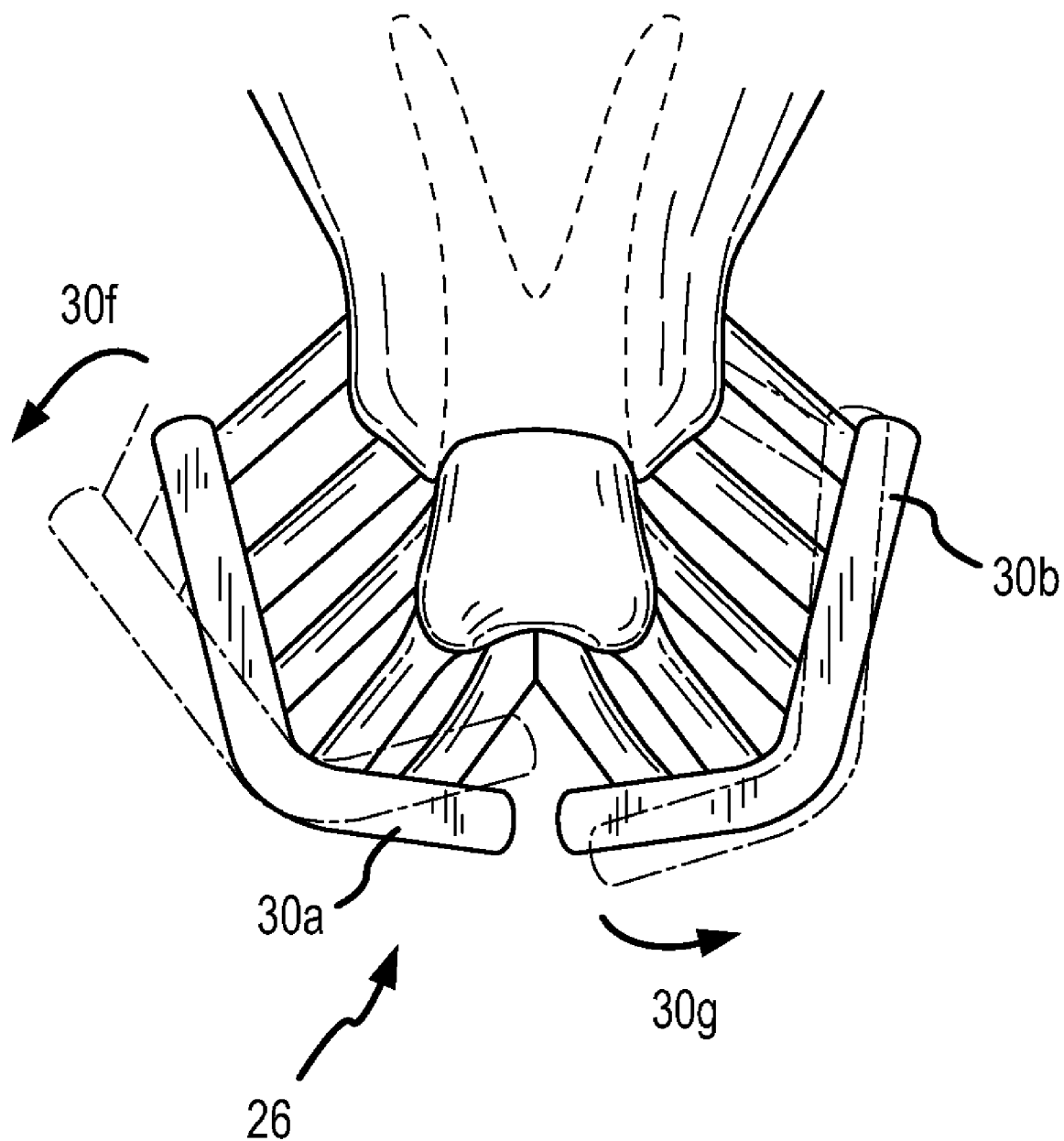
Figure 5C:
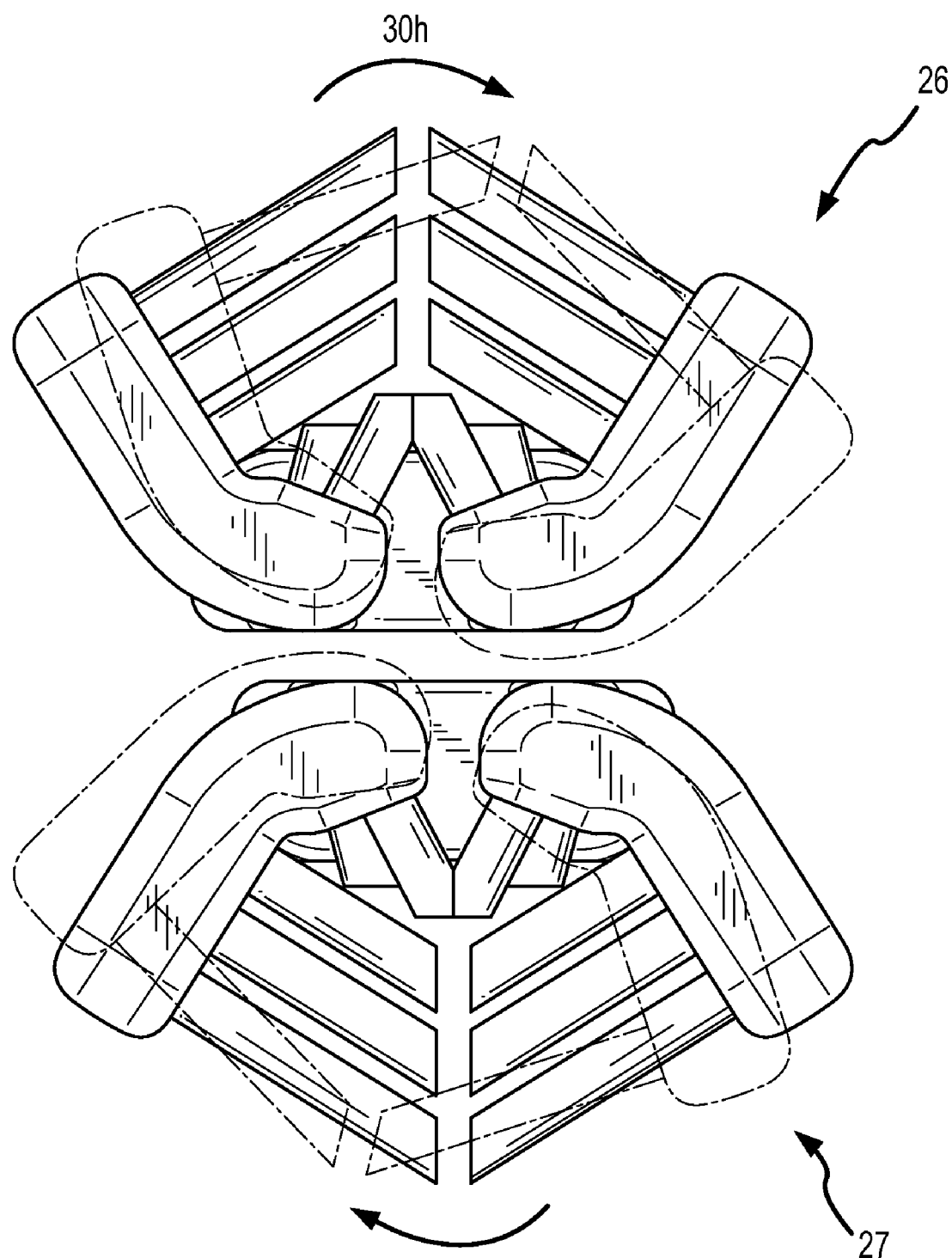

A swiveling positioning may include such resiliency, allowing relatively independent twisting or rotation of one or the other or both of the arms upon encountering an obstruction. This is shown in FIG. 5B (rotational arrows 30f and 30g). Moreover, as described in further detail below, a swivel positioning may include the swivel of the whole head assembly right and/or left, and if two heads are used then the swivel may be of both heads substantially simultaneously, see clockwise rotation/swivel 30h in FIG. 5C. Rotation is available for each of the head assemblies 26, 27 about the respective shafts 22a, 22b (FIGS. 1-3) on and to which the assemblies are mounted. Self positioning of these sorts may thus provide for easily and substantially automatically obtaining and maintaining the Bass position for teeth and for simplifying use in manipulation of the handle 21 for the human user and reducing or eliminating human error.

In use with two or four wrap-around brushes, such as one or as shown, two brushes in the first brush assembly 26 which here may be for the top teeth and/or one or two in the second brush assembly 27 which here may be for the bottom teeth, the user may simply bite into the brushing heads 26, 27, and self-positioning may be substantially automatic as the brushes position themselves or are otherwise positioned to substantially correctly contact tooth and gum surfaces (see FIGS. 4 and 5), any deviation accounted for by the resilient arms and/or the swiveling heads (see FIG. 5, e.g.). Alternative side-to-side or other orally effective relationships of brushes 26, 27 may be used instead. Thus, the brushes can achieve the ADA recommended Bass technique placement of bristles on teeth and gums, with the side contacts being at approximately a 45 degree angle (see FIG. 4A) or otherwise as may be desired. Each brush unit 26, 27, e.g., may have user specific dimensions, or may, due to the self-positioning described here, be fit for use in any user's mouth for bristle contact of every to-be-cleaned surface of the user's teeth and gums and may provide interproximal, gingival and/or sub-gingival contact while assuring that the brushing action does not include an overly aggressive bristle force. Such self-positioning may be achieved substantially automatically with or without the user's knowledge, understanding or active participation, as it is the width of the tooth or teeth which, in limiting the amount of resiling of the brush arms and/or heads, is actually achieving the self-positioning.

Another part of the ADA Bass techniques recommendation is to reciprocate the brushes in short (e.g. tooth-wide or less than about 0.25 inches, or in some cases between about 0.18 and about 0.25 inches), quick, back and forth strokes while applying light pressure in the direction of bristles. Note, such short strokes avoid the sweeping scraping which can lead to trenching (up and down strokes were once taught in an effort to avoid trenching); but, further such linear in and out strokes provide better cleaning. The bristles can bend and/or flex and move little, yet still bring sufficient action to bear upon and clean or dislodge debris. Accordingly, the device 20 hereof can, and in many preferred implementations will be adapted to provide a defined stroke that imparts an alternating brushing, as shown in FIG. 4B, for example, with a first stroke 53 in a first direction with a return in the opposite direction, and preferably here, one brush assembly, e.g., assembly 26 moving in the first direction 53 while a second brush head, e.g., assembly 27 is moving with a second stroke 54 in the other direction. The alternating stroke (out-to-in of one assembly simultaneously with in-to-out of the other assembly) is desirable for a variety of reasons, these reasons and exemplar sub-assemblies adapted to provide such strokes are described further below. It has been found that approximately 650-850 strokes per minute may provide the most effective results. Such speeds can be highly desirable, particularly as the strokes provide enough time for the bristles and particularly the bristle tips to react resiliently to move from one location to another and then have their bristle tips strike at debris trapped in a space, e.g., interproximal space 55 between the teeth, see e.g., teeth 56, 57 (FIGS. 4B and 4C) which debris might then be trapped at or near the mid point and thereby loosen the debris more efficiently with a back and forth action so that the debris may be cleared therefrom. Shorter strokes (less than or equal to about 0.25 inches) and slower speeds such as these (650-850 strokes per minute as compared with or opposed to 3 to 30 thousand (3-30 k) strokes per minute of some conventional power brushes, e.g., so-called sonic brushes) are also more gentle, providing massage-like contact as opposed to dental drill-like, high-impact speeds.

Note also, in some implementations, it may further be desirable to optionally though not necessarily include use of a dentifrice, tooth paste, flavor concentrate etc. To do this, the dentifrice may be delivered with, i.e., added to the brush or brush bristles in substantially conventional fashion and thus move with the brushes into the user's mouth and thereby be applied to the teeth and/or gums.

Figure 6A:
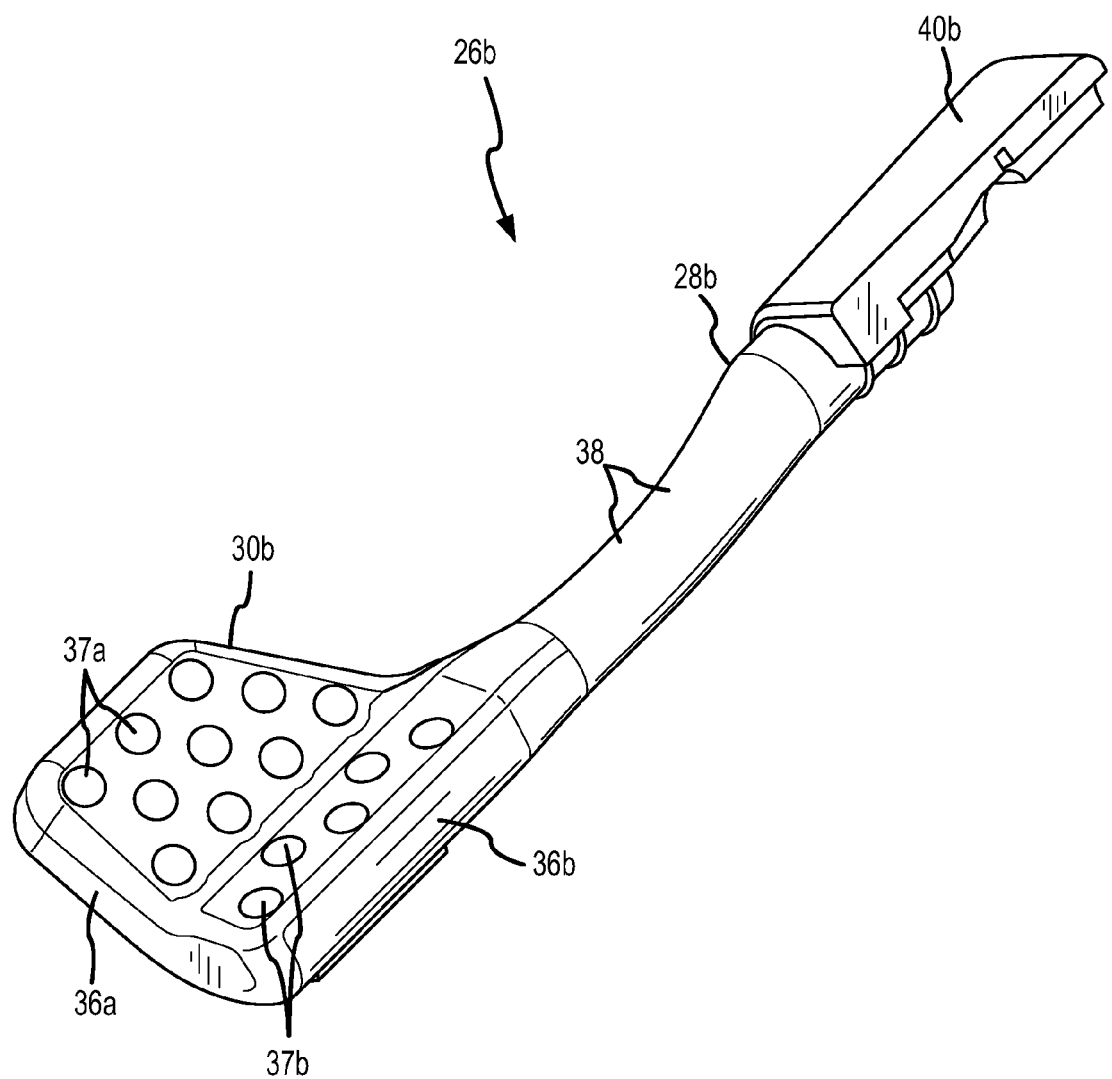
FIG. 6, which includes subpart FIGS. 6A, 6B, 6C, 6D, 6E and 6F, provides respective isometric individual part and/or exploded views of a brush assembly of an oral cleaning device like those in FIGS. 1-5.
Figure 6B:
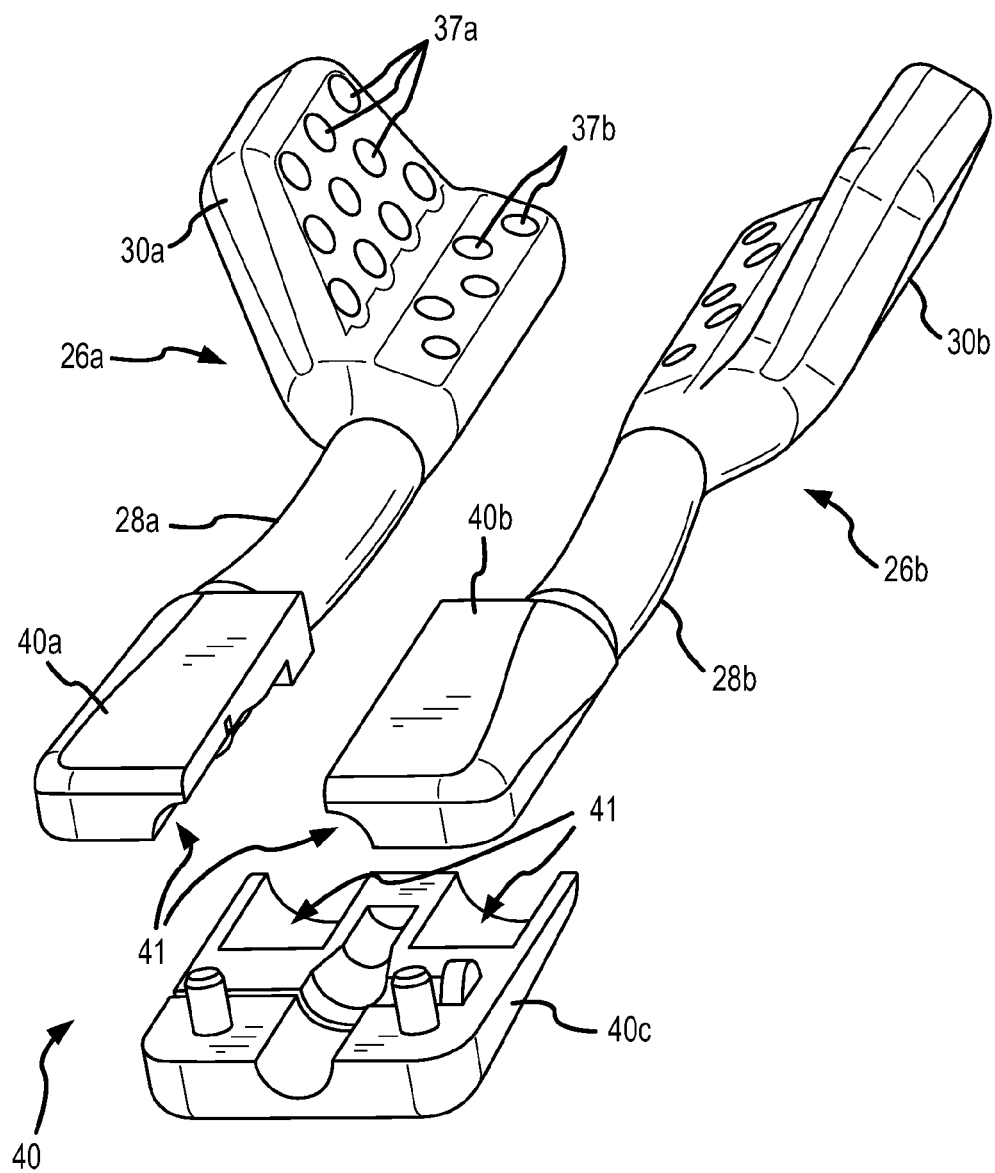
Figure 6C:
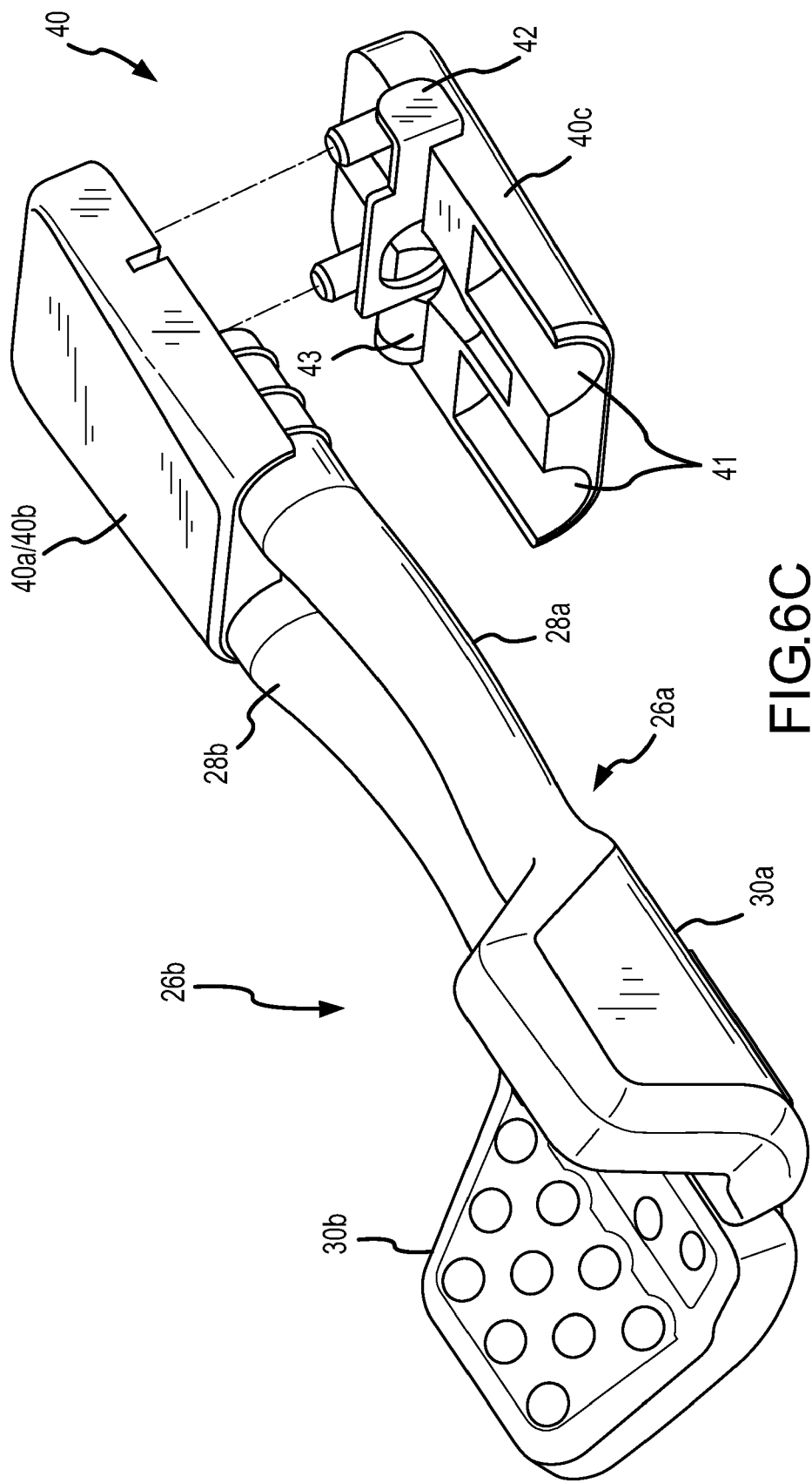

The respective brush assemblies 26, 27 introduced and shown above, may be unitary appliances (e.g., the one brush head 30 or 31 including the side and crown brush portions 36a, 36b), or may as shown in FIG. 6, be respective assemblies of one or more brushes, as for example the brushes 26a and 26b of FIG. 6 (see the individually-depicted brush 26b of FIG. 6A and the respective combinations of brushes 26a and 26b of FIGS. 6B and 6C). Each of these brushes may in turn, also as shown and described above, each include arms 28a, 28b and heads 30a, 30b. Note, as identified in FIG. 6A, it may be desirable to include a relief, reduction and/or other curvature feature 38 in the arm(s) 28 to avoid undesirable impact of an arm 28 on/with the teeth in use. The heads 30a, 30b, may also have respective head portions 36a, 36b (side, crown) (see also FIG. 3) with respective drill holes 37a, 37b (side, crown) to receive respective tufts 32a, 32b (side, crown) of bristles 34, 35 (tufts 32a, 32b shown and identified in FIGS. 3B and 3C).

The respective brush assemblies 26, 27 may also include respective brush bases 40 (see the respective assembled base 40 in FIG. 3A as well as the parted components of bases 40 in FIGS. 6B and 6C) for connection of the respective brushes together, and/or for connection of the brush assemblies to the control handle 21 and/or shafts 22. The bases 40 may be initially separate devices or may as shown in FIG. 6 be separate portions 40a, 40b and 40c formed as separate parts, portions 40a and 40b formed as integral parts of the respective brushes 26a and 26b and portion 40c as a separate base piece. A variety of connection features 41 (e.g., posts and/or receiving holes therefor) may be included within the various portions 40a, 40b and 40c to provide for the connection of the brush portions 40a, 40b and 40c together. These portions may then be connected by snap fit, snug fit, friction fit or welded, e.g. sonically-welded, or glued or otherwise adhesively or cohesively or otherwise put and held together.

Figure 6D:
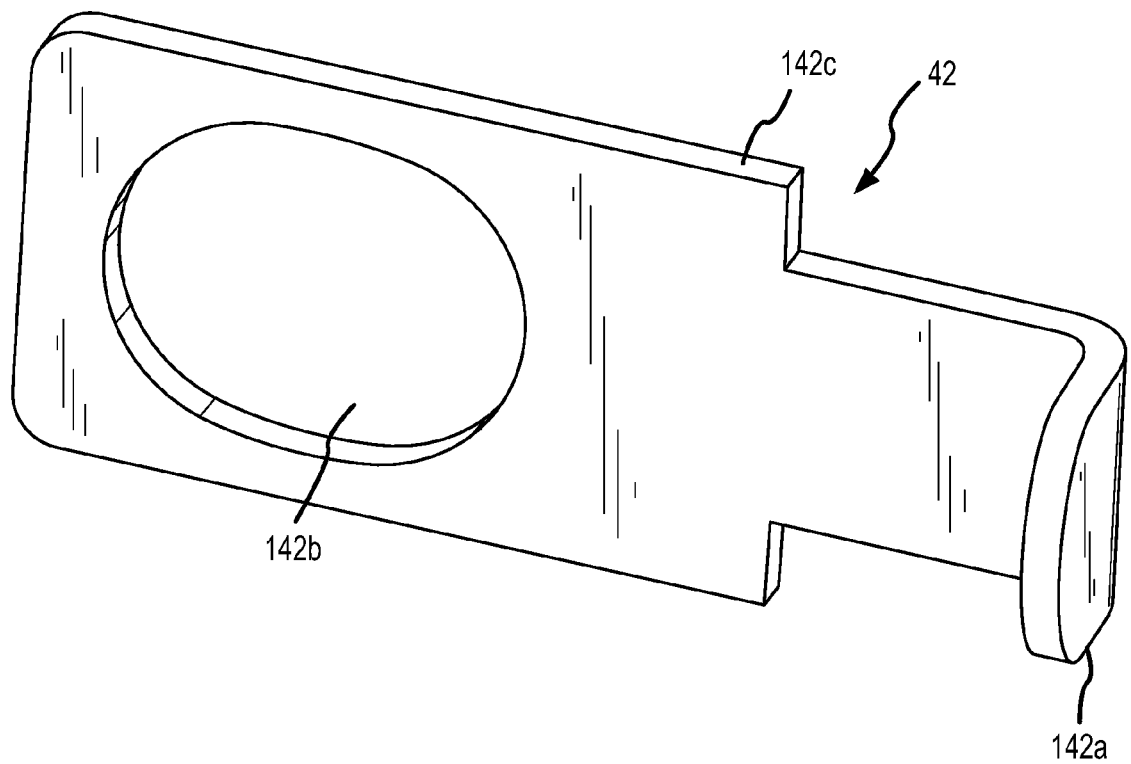
Figure 6E:
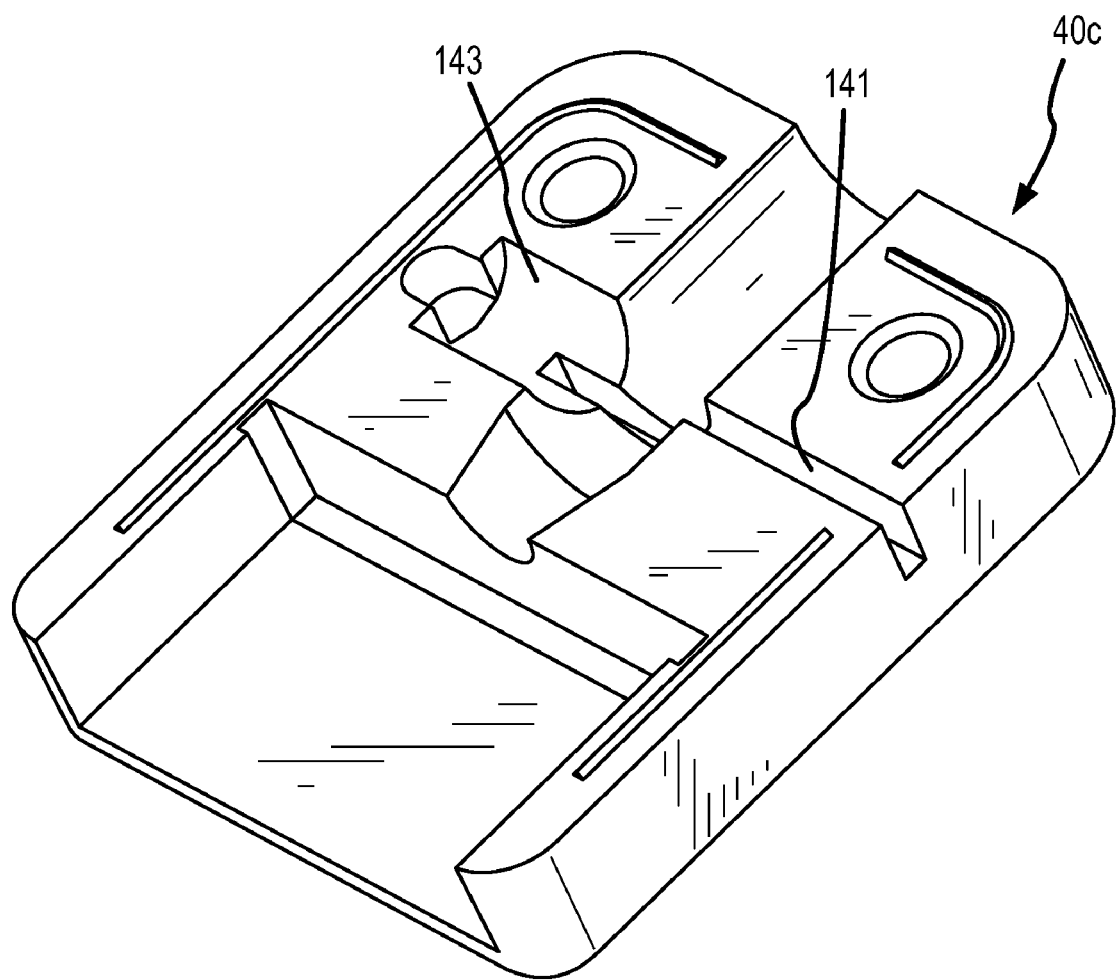
Figure 6F:
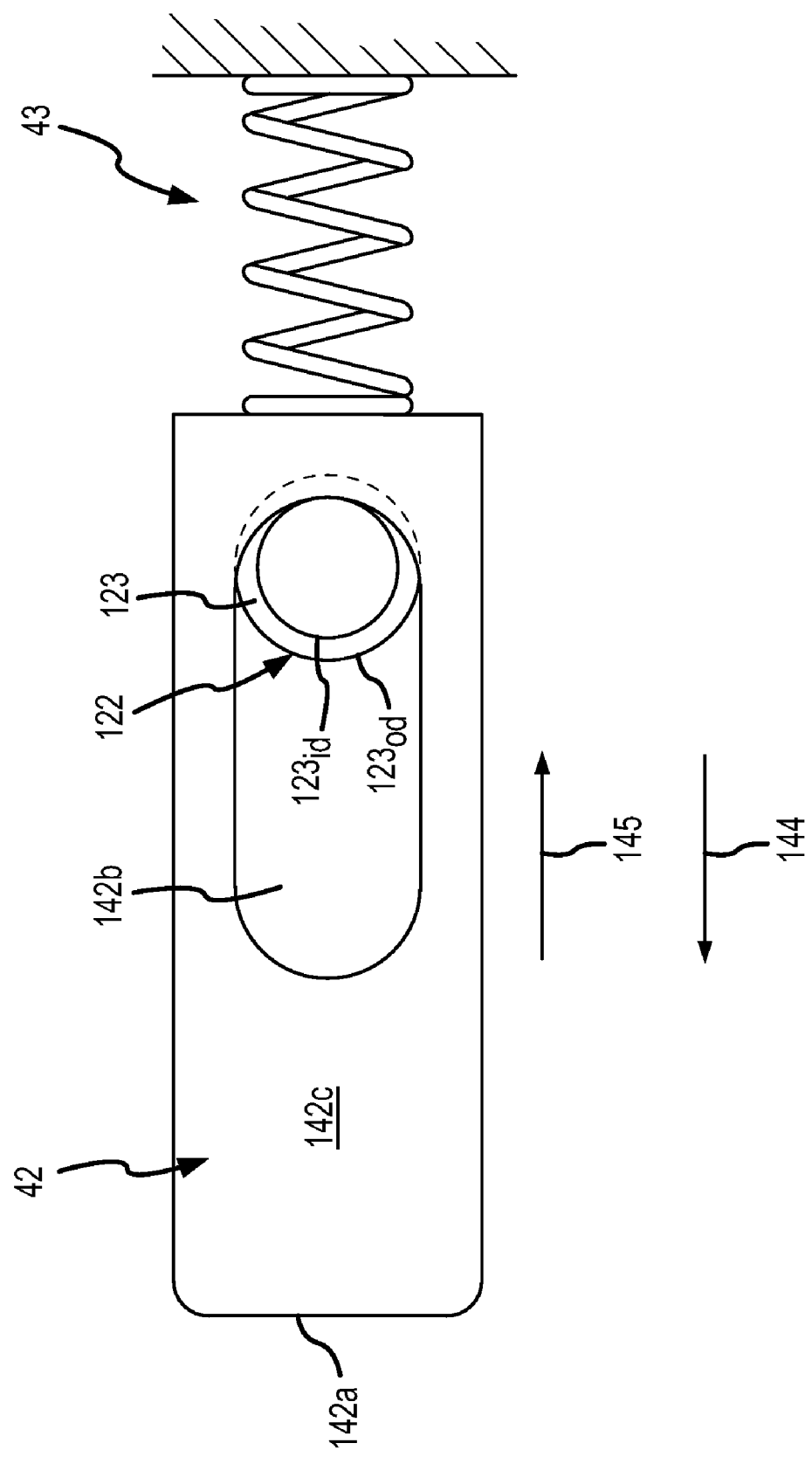

As shown in FIGS. 6C, and 6D, a push-button device 42 may be included within the base 40 within its own slot 141 defined in one or more of the base portions 40a, 40b and 40c. The push button 42 may preferably be spring-loaded counter the release direction, as by a spring 43 (shown schematically in FIG. 6F) adapted to be disposed in a spring feature 143 in the base 40. The push button device 42 may have a push button surface 142a to be disposed outside the base 40 and connected hereto, an internal structure 142c with a cutout feature or ring 142b here shown as a sort of elliptical cutout. As shown in FIG. 6F, the push button device 42 may be engagable with the quill end 122 of a shaft 22, e.g. shaft 22a (see FIGS. 7A and 7B). The quill end 122 may have a slot or notch 123 with inner and outer diameters 123id and 123od (FIG. 6F) which together define the slot. Engagement as shown in FIG. 6F may then be had when the edge of the cutout feature 142b clips into the slot 123, and the spring 43 resiles back in the direction 144 under its spring force.

Disengagement of the quill end slot 123 from the cutout feature 142b may be effected by pushing on the push-button surface 142a in the direction 145 against the bias of the spring 43 which then allows for the outer diameter 123od to enter and move through the cutout feature 142b thereby allowing for removal of housing 40 and brush assembly 26 (or 27) from the shaft 22. Opposite engagement may be had by pushing the housing 40 onto the shaft 22 such that the quill end thereof enters the cutout feature 142b and the ramp surface 122r of the quill end engages the cutout feature and causes movement thereof against the bias of and compressing or otherwise deforming the spring 43 as the edge of the cutout feature rides along the incline of the ramp until the slot 123 is reached at which point the spring 43 pushes back against the push-button device 42b to engage the edge of the cutout feature with the slot as shown in FIG. 6F.

The tooth brush assemblies 26, 27 may thus be removably mountable on the shafts 22 and thereby replaceable if and/or as they may be spent, or the assemblies 26, 27 may be interchangeable so that each of a plurality of users may each also have his/her own brush heads for sanitary reasons. Alternative cleaning head assemblies (see FIG. 10, or others not shown) may be interchangeably used herewith as well. Or, different sizes may be made available (for plural or singular users), e.g., smaller brushes can provide a better fit around particular teeth, or for particular users, smaller brushes perhaps being more comfortable as well, and/or providing fewer bristles and thus reduce bristle interference.

Moving shafts for moving the cleaning heads 26, 27 will now be described. For example, in FIGS. 2 and 7 (including FIGS. 7A, 7B and 7C), are depictions of isometric cut-away views of alternative handles 21 of exemplary units 20 which each provide for moving one or more cleaning assemblies 26, 27 on respective shafts 22a, 22b of a connection assembly 25. More particularly, the structural shafts 22a, 22b may be disposed in reciprocal motive disposition in and emanating from the control handle 21. Note, the shafts 22a, 22b may be relatively integral or contiguous with or otherwise as shown and described above, may be connectable with brush assemblies 26, 27.

Figure 7A:
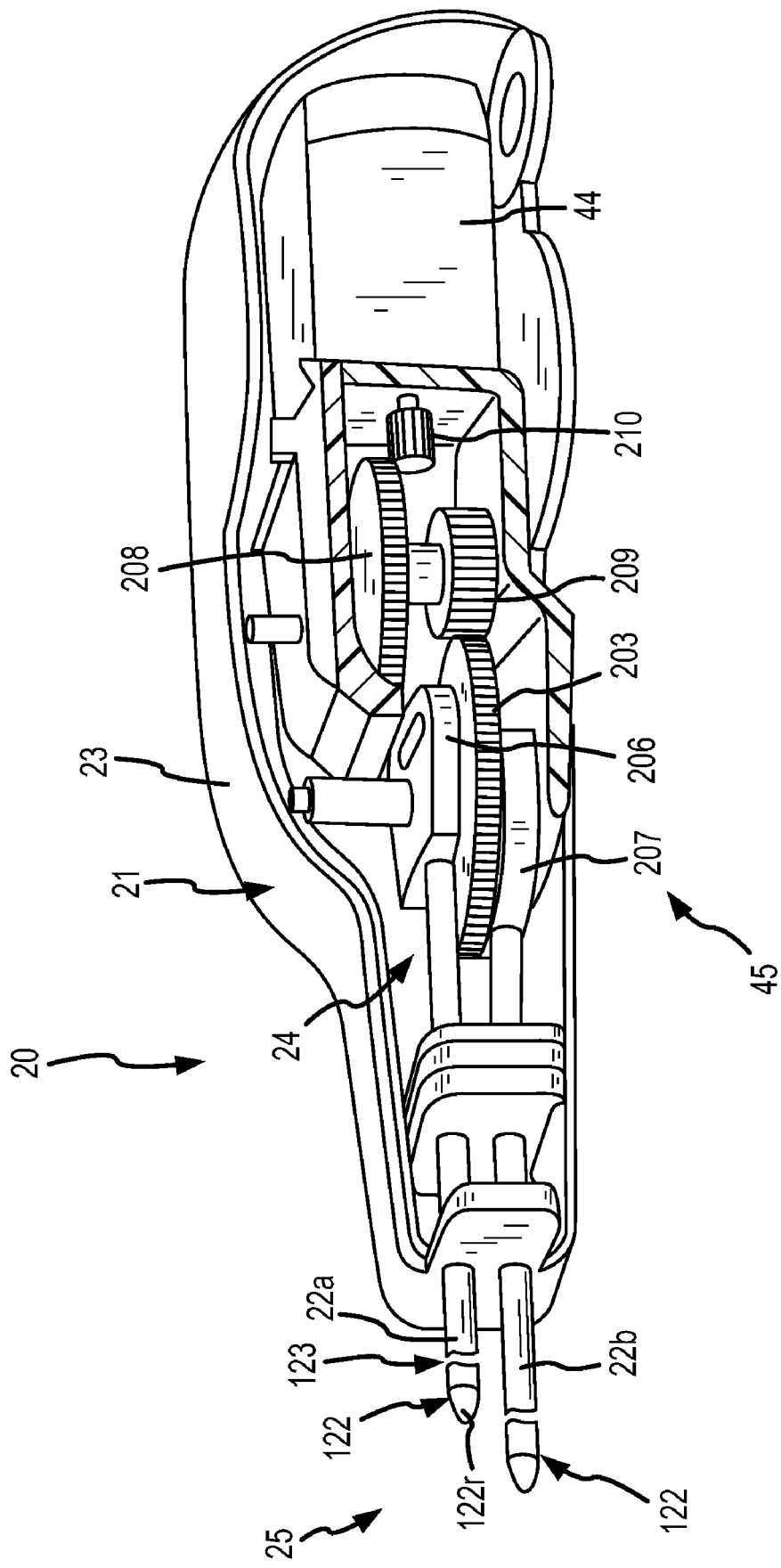
FIG. 7, which includes subpart FIGS. 7A, 7B and 7C, provides respective cut-away isometric and elevational views of exemplary oral cleaning devices according hereto.
Figure 7B:
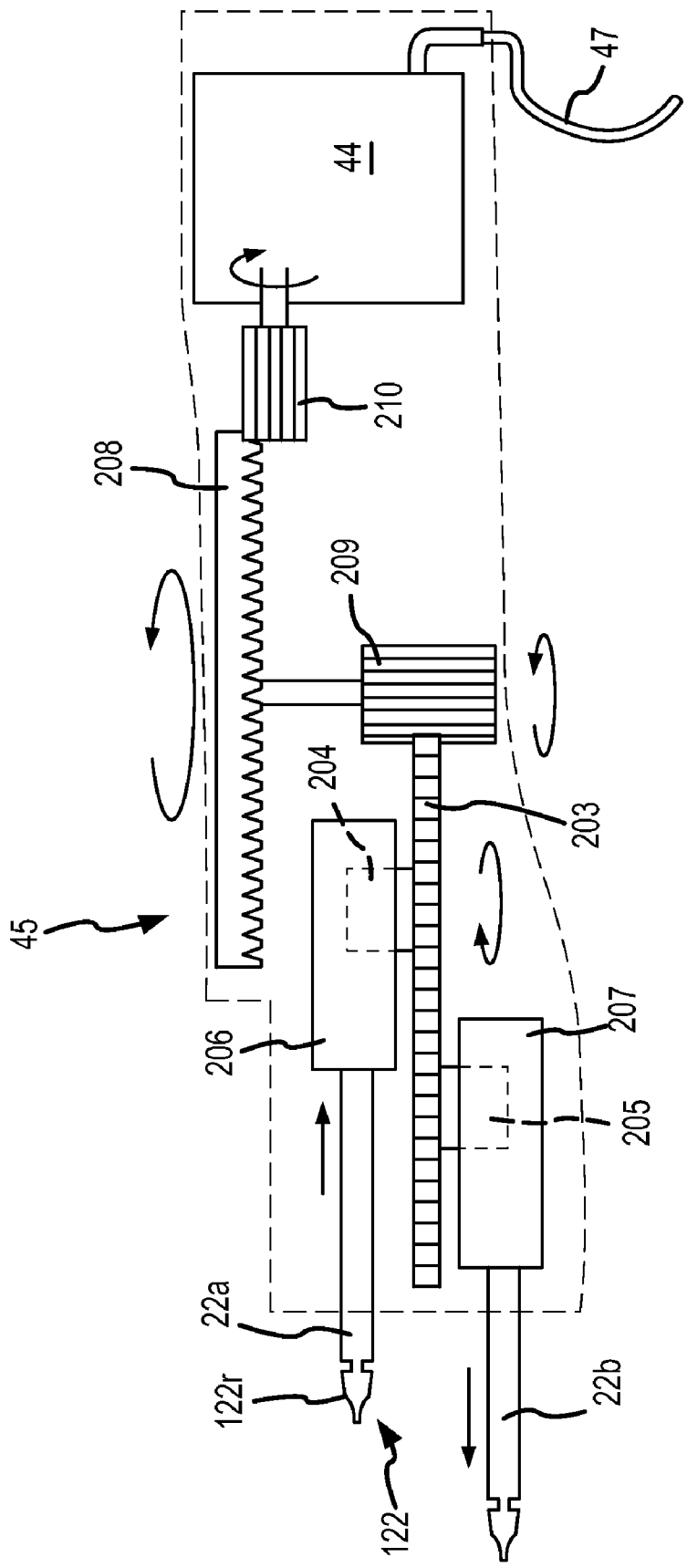
Figure 7C:
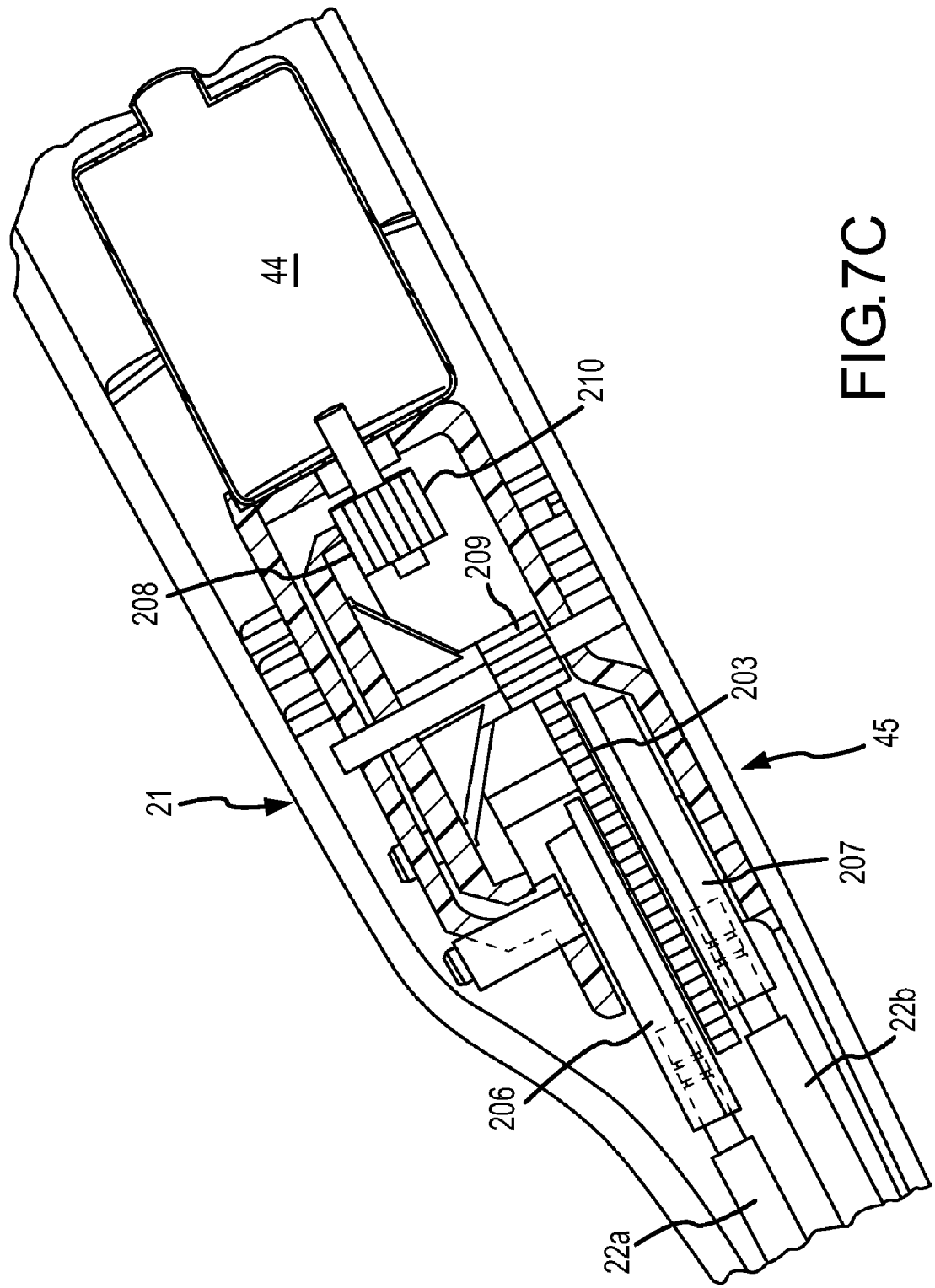
Figure 8A:
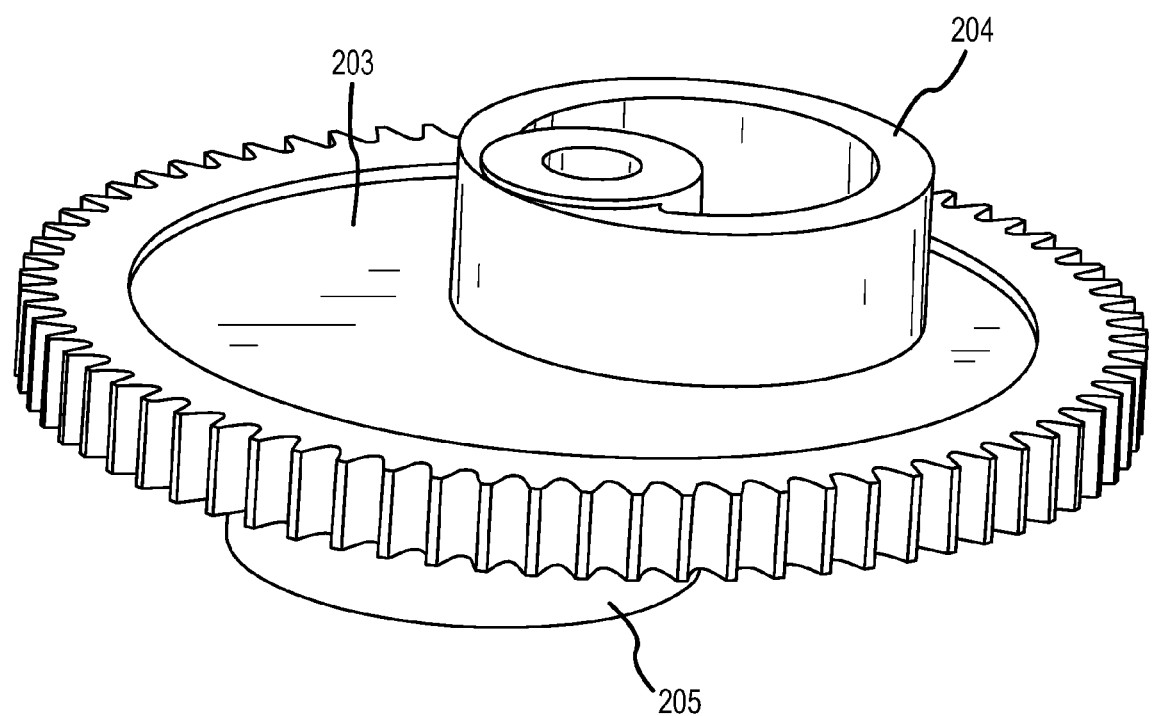
FIG. 8, which includes subpart FIGS. 8A, 8B and 8C, provides respective isometric views of exemplary interior components of a device according hereto.
Figure 8B:
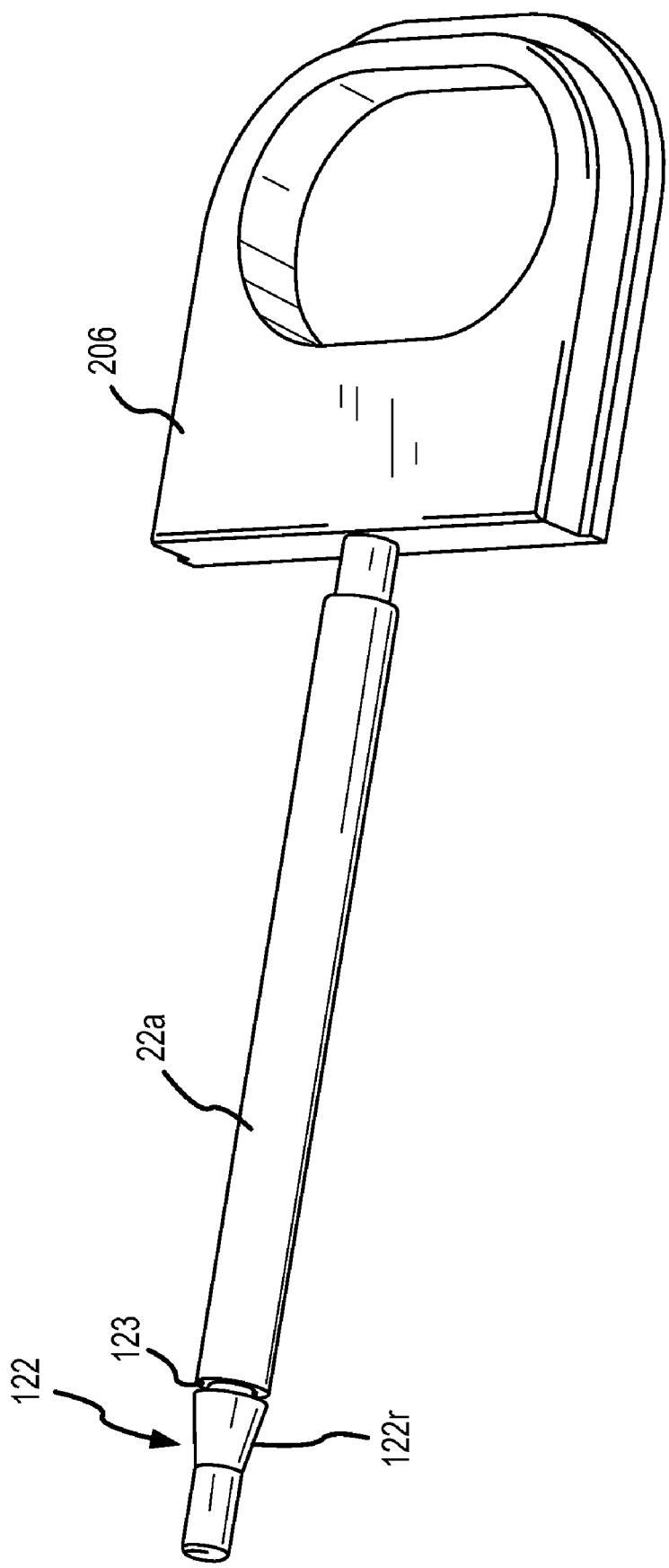
Figure 8C:
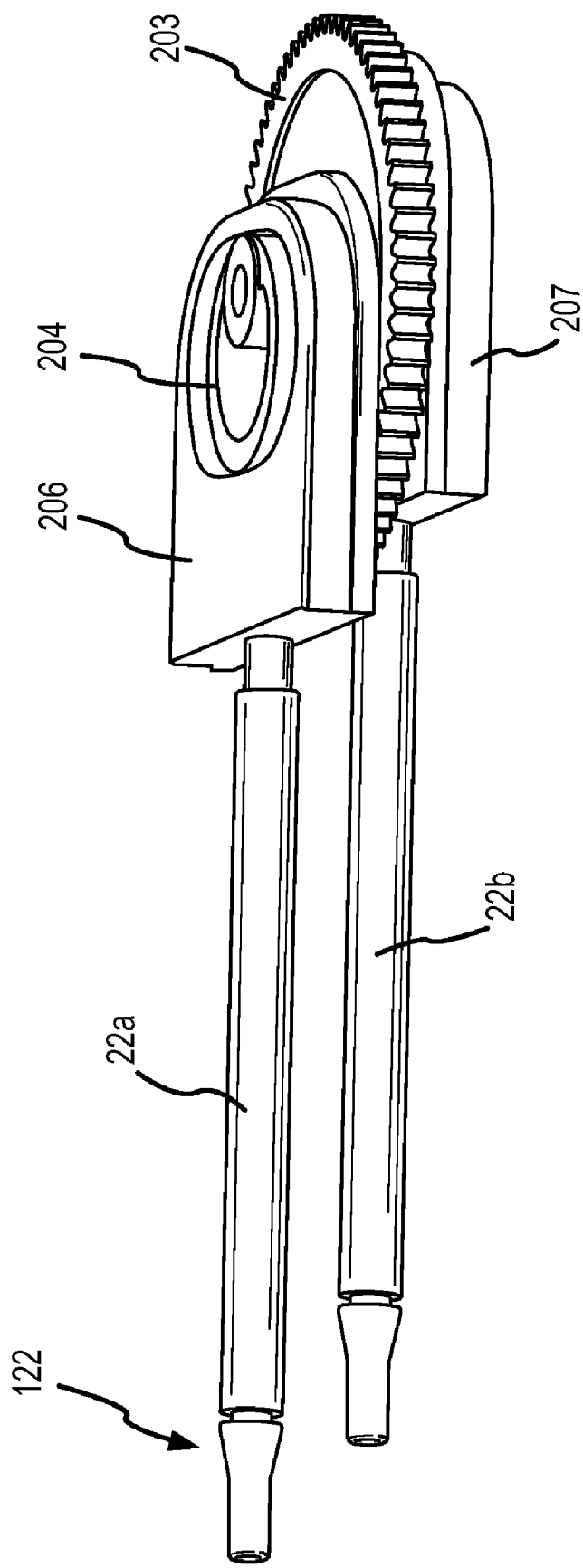

Inside the control handle 21 may be one or more control assemblies 24 which may include conventional or unconventional reciprocation hardware. As a first example, a direct current (DC) motor 44 may be included to provide primary power to reciprocate the brush head assemblies 26, 27. The motor 44 may activate a mechanical system 45 such as a system of gears, to ultimately move the cleaning head assemblies 26, 27. The system 45 may be a double reciprocal/opposing movement like that described and shown in FIGS. 2 and 7 which may include mechanisms like a crown gear 208 connected by a shaft to a reduction spur gear 209 which communicates in gear meshing relationship with a double cam gear 203 (see FIGS. 7A, 7B and 7C). The DC motor 44 is adapted to directly turn a pinion gear 210 which in turn, turns the crown gear 208 and thence gear 209 is turned and turns the double cam gear 203. The gear 203 has respective cams 204, 205 one each on opposite sides of the gear 203 (see FIGS. 7 and 8 (8A, 8B and 8C). The upper first side cam 204, the double cam gear 203, and second side cam 205 may be separate parts or may all be combined as one piece. Structural shafts/arms 22a and 22b may be attached to cam followers 206, 207 (FIG. 8). The double-cam big gear 203 which may thus by contact move the two cam followers 206, 207 to move in and out the shafts 22a, 22b relative to the power handle 21. Thus, this causes the structural shafts 22a, 22b to reciprocate in opposing directions and thereby provide for alternating dispositions of the heads 26, 27, the positions and directions being substantially and reversibly in opposition such that at one moment, the heads are as shown, and then they may be reciprocated such that they switch relative positions inside the mouth. FIGS. 7A and 7B show one position where the shaft 22a is further retracted within the handle 21 while the other shaft 22b is extended. A switched position is shown in FIGS. 1 and 2 where the upper first side shaft 22a is extended and the other shaft 22b is retracted. The shafts 22 thereby further provide this reciprocatable linear movement to the brush head assemblies 26, 27 to alternately move into and out of the oral cavity in order to desirably clean the teeth and/or gums.

Note, the two top heads 30a, 30b on the brush assembly 26 may as shown preferably be reciprocated together and the other, lower two heads 31a, 31b of the brush assembly 27 may be reciprocated together in opposed relationship to the upper heads. In many cases with devices 20 it will be preferable to provide such alternate reciprocal moving part implementations having respective opposing parts moving contrary to each other to provide balance to the overall device. In many implementations, the force balance of alternating reciprocation can provide for a static handle at the same time as the brushes are dynamically cleaning. In any two opposed brush orientations, the opposing brushes may be moving substantially simultaneously in opposite directions, one out while the other is moving in and vice versa. Reciprocation of top and bottom (and/or side to side or other arrangement) in opposite directions provides substantially simultaneous action and reaction in and out, and this force action and reaction cancels each other out so that net motive force on the handle 21 is substantially zero and the handle 21 thereby remains stationary. The mechanical force counterforce, i.e., the force(s) tending to push the brush heads further in, or out of the mouth simultaneously provide at least a reduction of the overall forces felt by the user who may then be able to operate the device simply by and through the use of a simple/minimal grasp of the handle 21 with the thumb and forefinger. This overall action/reaction may also provide a further advantage in the self-positioning described above, overcoming the reciprocal brushing action to allow the brush head and bristle design to achieve and maintain the desirable self-position (FIGS. 3, 4 and 5) unforced away therefrom by the motor driven reciprocation. Also in these and/or other two (or more) brush implementations, though at least two such brushes may move in opposing reciprocation together, it may be possible to have contrary alternating movements whether for relative top and bottom movements contrary side versus side movements.

As mentioned above, the device 20 can provide alternating brushing, with, as shown in FIG. 4B, a first stroke 53 in a first direction with a second stroke 54 in the other direction. And, approximately 650-850 strokes per minute may provide the most effective results. Such alternating stroke speeds can be highly desirable as the strokes may have enough time for the bristles to react resiliently to move from one location to another and then strike at debris trapped in a space, e.g., interproximal space 55 between the teeth, see e.g., teeth 56, 57 (FIGS. 4B and 4C) which debris might then be trapped at or near the mid point and thereby loosen the debris more efficiently with a back and forth action so that the debris may be cleared therefrom. Slower speeds such as these (650-850 strokes per minute as opposed to 3 to 30 thousand (3-30 k) strokes per minute of some conventional power brushes, e.g., so-called sonic brushes) are also more gentle, providing massage-like contact as opposed to dental drill-like, high-impact speeds. Note, many other conventional power brushes boast high speeds, often spinning actions of 4,000 rpm and more, speeds that can create a feeling of discomfort. The slower speeds preferred here, on the other hand, rely on accurate bristle positioning to obtain effectiveness, and as a result, the brushes can reciprocate at a fraction of the speed of other products, resulting in user enjoyment of a comfortable massage with every use. Note, multiple or multi-speed options may alternatively be made available in these or other ranges of strokes per minute. In many cases, one speed is acceptable, but optionally one or more slower speeds can be offered particularly for beginners to become accustomed to the action. Faster speeds may also be offered.

An assembly such as this may be adequate for twin cooperative goals of efficaciously brushing the occlusial and lingual-bucal surfaces of the teeth and gums (including gaps between such surfaces and/or between the teeth and gums) while also simultaneously brushing the aforementioned surfaces and also the underlying gums. An aspect hereof may thus be the provision of an improved powered toothbrush for simultaneously efficaciously brushing the occlusial and the lingual bucal surfaces including any gaps therebetween while simultaneously beneficially brushing the teeth surfaces and also the underlying teeth/gums, the latter benefit representing therapeutical prevention of periodontal problems.

Figure 9A:
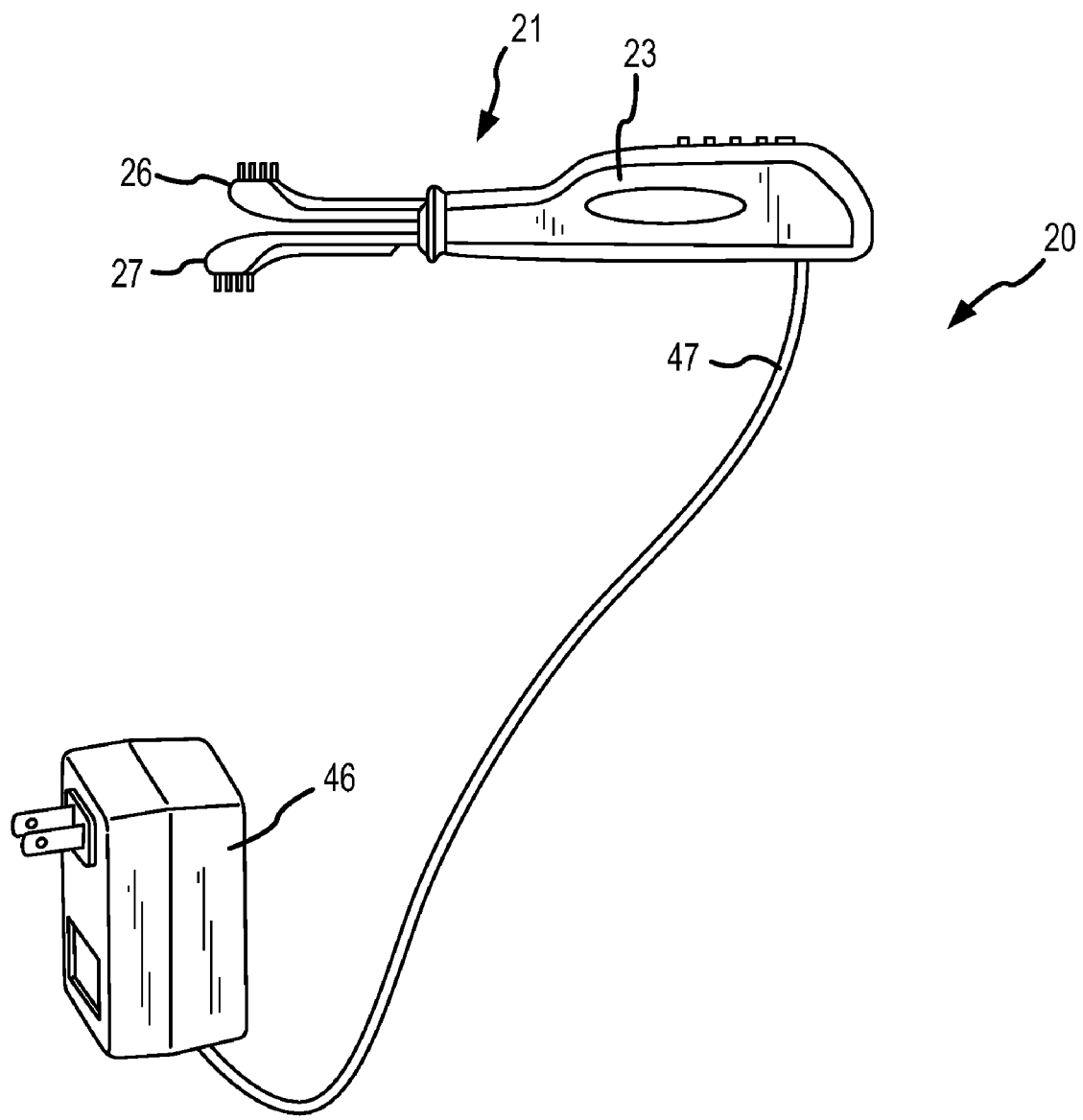
FIG. 9, which includes subpart FIGS. 9A, 9B and 9C, provides respective isometric views of a system hereof and/or parts thereof.

Note, shown in FIG. 9 is a schematic representation of a system 20 including a brush control module 21 with a power unit 46 and a power cable or cord 47 connected therebetween for plugging into a wall socket, for an example. The control handle 21 may either be hardwire connected or may more preferably be rechargeable (e.g., rechargeable batteries or induction charging mechanism(s), not directly shown) and thus operated without a power cable 47 and external power source 46. A remote charger or induction charging unit would then be used, and in such a case the representation in FIG. 9A could be indicative of the disconnectable connection for recharging. In some implementations on this scale, a recharger may provide a multiplicity of operations, as for example up to 50 times, or up to a month, e.g.

Figure 9B:
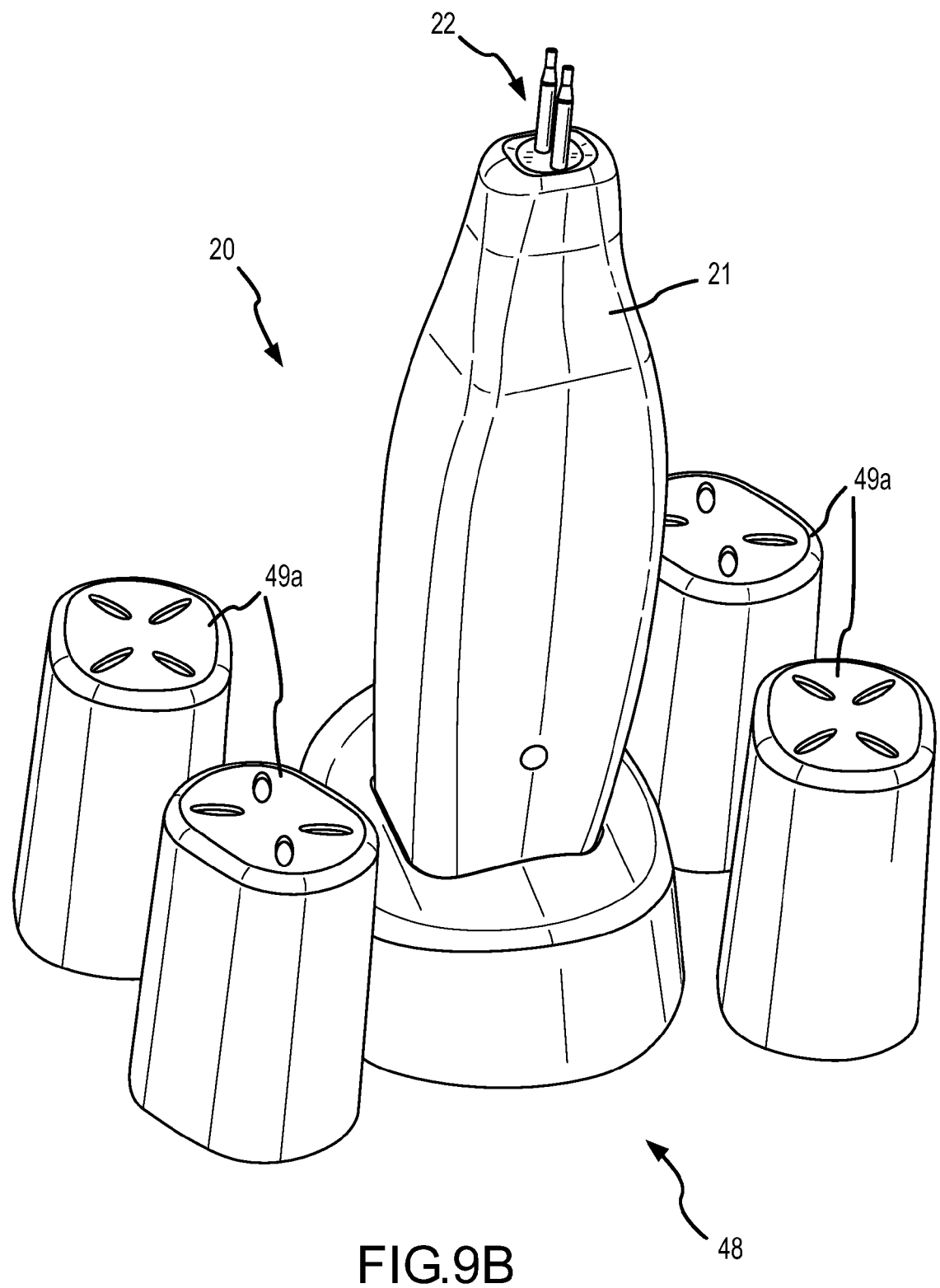
Figure 9C:
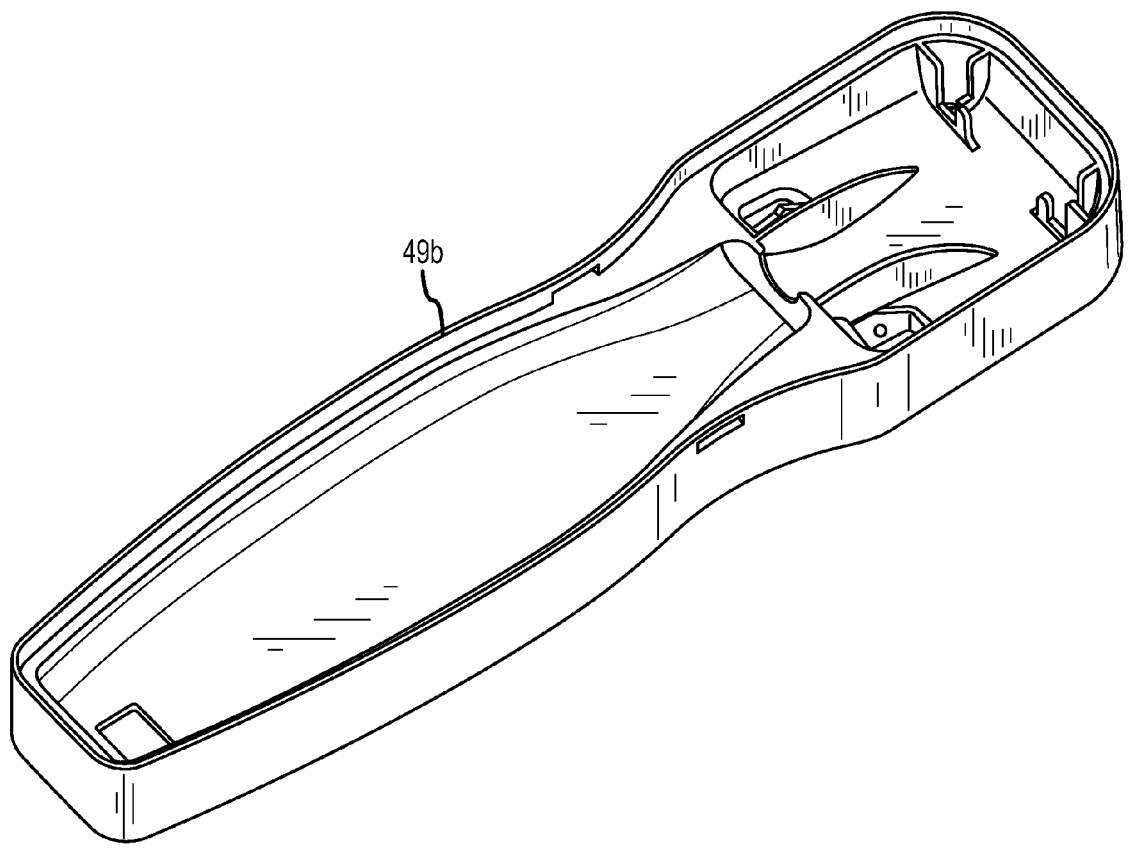

Other repowering connections may also be had, as for example, including non-rechargeable, but replaceable batteries or where the recharger is built into the handle 21 or involves a table top recharging stand 48 for placement of the handle 21 therein as illustrated generally in one exemplar implementation of FIG. 9B, such being adapted to rest on counter-top or other surfaces. Also shown in FIG. 9B are several brush cases 49a for holding, temporarily, brush assemblies 26, 27 to be connected to a handle 21. A further alternative handle case 49b (top not shown) is shown in FIG. 9C, in which a handle 21 may be made to rest or otherwise be disposed in an storage location, as for example, horizontally on the counter, in a drawer or on a shelf, or, which may be adapted for portability, i.e., to carry the handle 21 thus making the device travel friendly (particularly with such devices having long re-charge options (e.g., 50 uses or a month's amount of uses)). Each of the cases 49a, 49b may preferably include air and/or drainage holes to allow breathing/drying and/or drainage of water away after use.

An alternative implementation, see FIG. 10 (including FIGS. 10A, 10B, 10C and 10D), may include alternative sub-assemblies 226, 227 including triple toothbrushes, see e.g., brushes 226a, 226b, 226c and 227a, 227b and 227c. or otherwise. Exemplary tripartite or other brush assemblies for use in alternative implementations like those shown here may also alternatively be like those disclosed in co-pending U.S. patent application Ser. No. 10/357,564 filed Feb. 5, 2003, and in PCT application No. PCT/US2003/01601, Publication No. WO03101365 (A1), both by at least one of the same inventor(s) as the present case. The disclosures of those applications are hereby incorporated herein by reference as if fully set forth here. More particularly, in this first alternative example, shown in FIGS. 10A through 10D, a brush device 20 may include a handle 21 as above, with one or more forwardly positioned brushing assembly(ies) 226, 227 for brushing lingual and bucal surfaces and occlussial surfaces of a row of teeth. Brushes like these tripartite brush assemblies 226, 227 can be used for brushing insides, outsides and topsides or crowns of the teeth substantially simultaneously, and may also be used to position the brushes in operative position and guide the brushes throughout the oral cavity for efficient usage. In this and various of the other toothbrush examples usable herein/herewith, as for example with the currently described tripartite brushheads 226, 227, these may be adapted to receive one or more teeth securely therein, and thereby position the device 20 such that the brushes 226a, 226b, 226c and 227a, 227b and 227c may be very advantageously aimed at the teeth and/or gums in strategic position to provide maximal cleaning. An angle of such cleaning may be such as to point the bristles at the gum line as suggested by various drawing figures herein, as in the particular examples of FIGS. 10A and 10C.

The brush combinations are optional, and/or interchangeable. A tripartite assembly 226 for example could include optionally one or more laterally spaced heads 226a, 226b and could further include a crown brush 226c. Similarly, a lower tripartite assembly 227 could include a crown brush 227c (this could be a sole brush, see e.g., brush 327 in FIG. 11, described below), and/or may optionally include lateral heads 227a, 227b. In such embodiments, the brush head assemblies could provide secure top to bottom and/or lateral, side to side positioning of the cleaning assembly(ies) 226 and/or 227 inside a user's mouth. All the user would need to do is bite down into the brush head assembly(ies), and thereby have the brushes adequately and potentially very accurately positioned for maximal cleaning. Moreover, here also, in order to effectively eliminate human error, these tripartite brushes may also "self-position" relative to the teeth and gums. As such, the six (6) brushes in the FIG. 10 implementation are pre-positioned to correctly contact tooth and gum surfaces. The user simply bites into the brushing head, and self-positioning is automatically provided in accordance with the ADA recommended Bass technique, placing a desirable proportion of bristles (e.g., one half (½)) on the teeth and another proportion of bristle tips (e.g., another one half (½)) on the gums at approximately a 45 degree angle. Note, positioning the brushes properly may be generically referred to using a guide means, here the arrangement of one or more brushes, which themselves lock around the teeth and correctly position the bristles. And, as above, the position of the brushes 226a-c and/or 227a-c here may also use/rely on the resilient spreading and/or squeezing movement of the respective heads 230a, 230b, 230c, 231a, 231b and/or 231c, that are connected by six respective resilient arms 228a, 228b, 228c, 229a, 229b and 229c to respective bases 240, and are connected by shafts/extensions 22a, 22b to handle 21 (see FIG. 10B, e.g.).

Figure 10A:
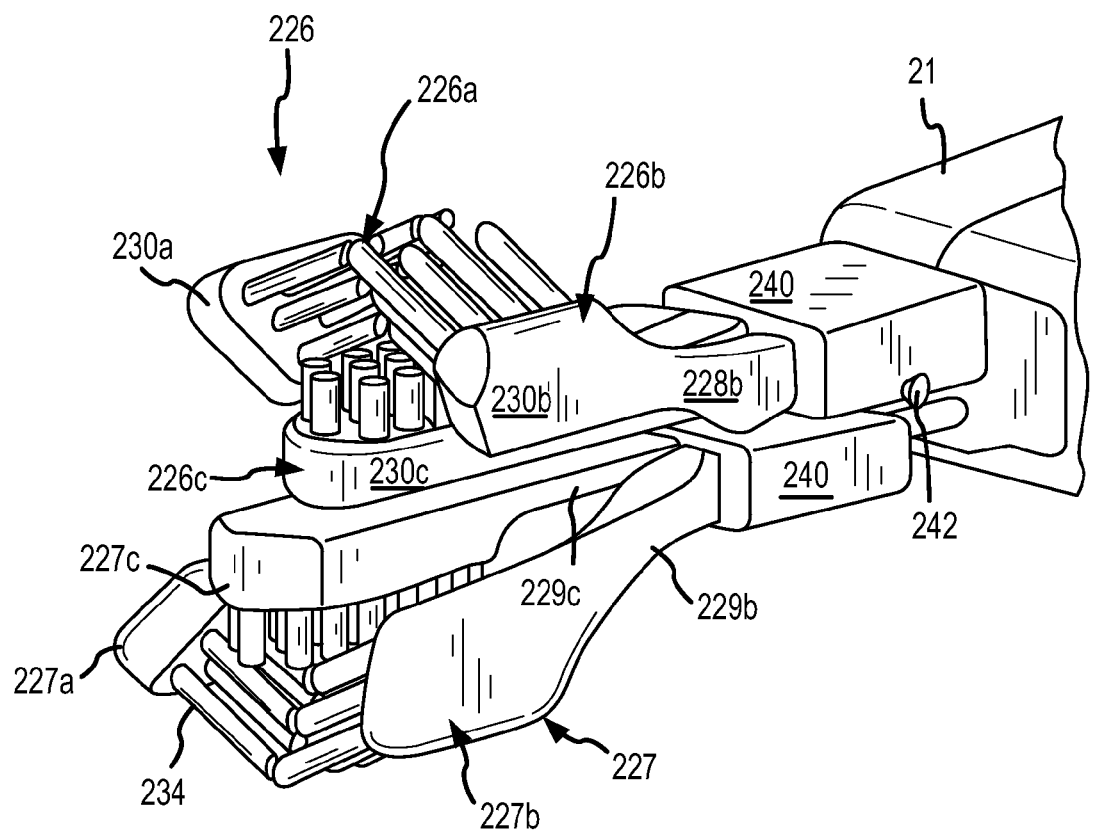
FIG. 10 is a collection, which includes subpart FIGS. 10A, 10B, 10C and 10D, of elevation, plan and isometric views of alternative brush assemblies for use with an oral cleaning device/system also according hereto; and, FIG. 11, which includes subpart FIGS. 11A and 11B, provides respective elevational views of exemplary alternative brushes according hereto.
Figure 10B:
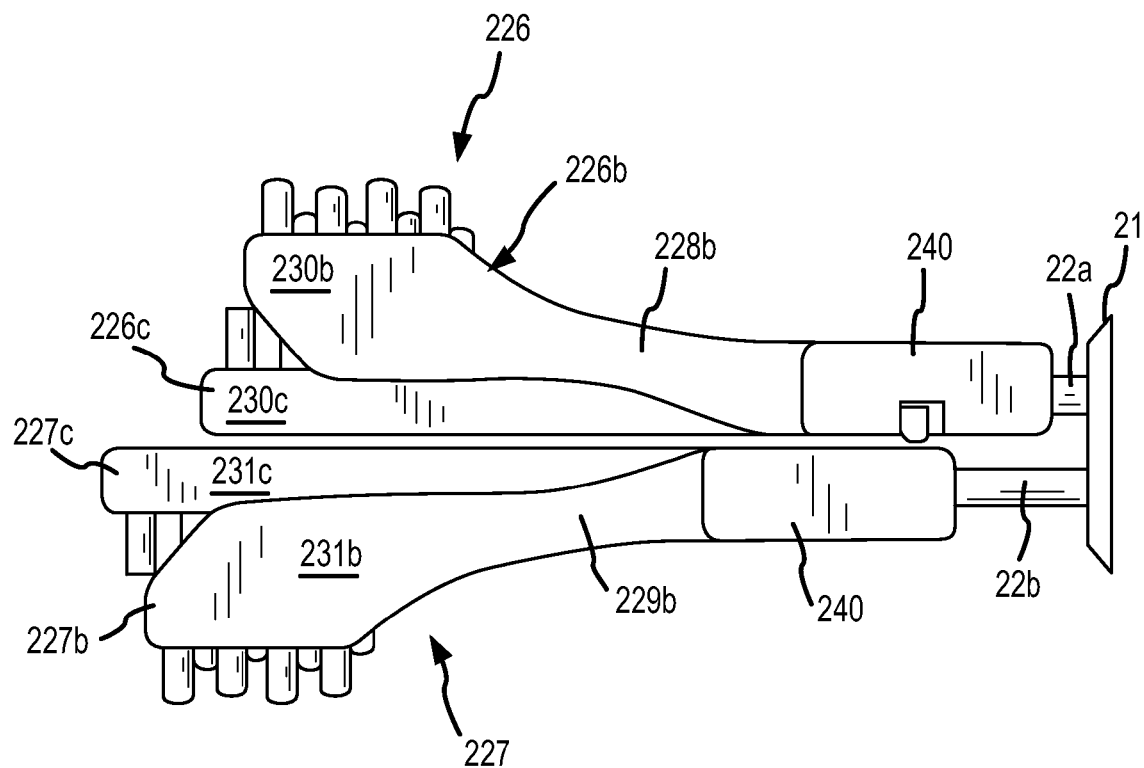
Figure 10C:
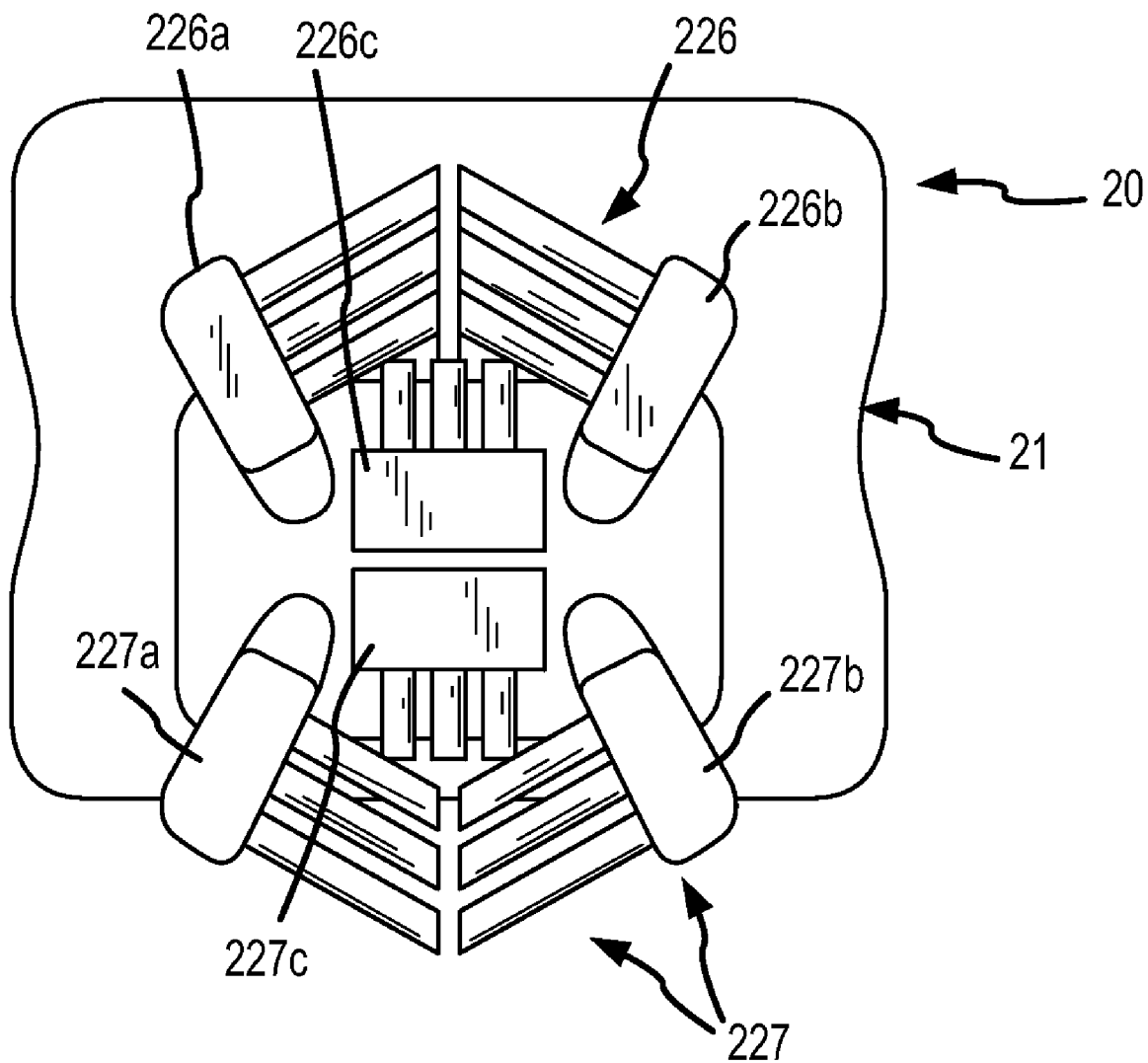
Figure 10D:
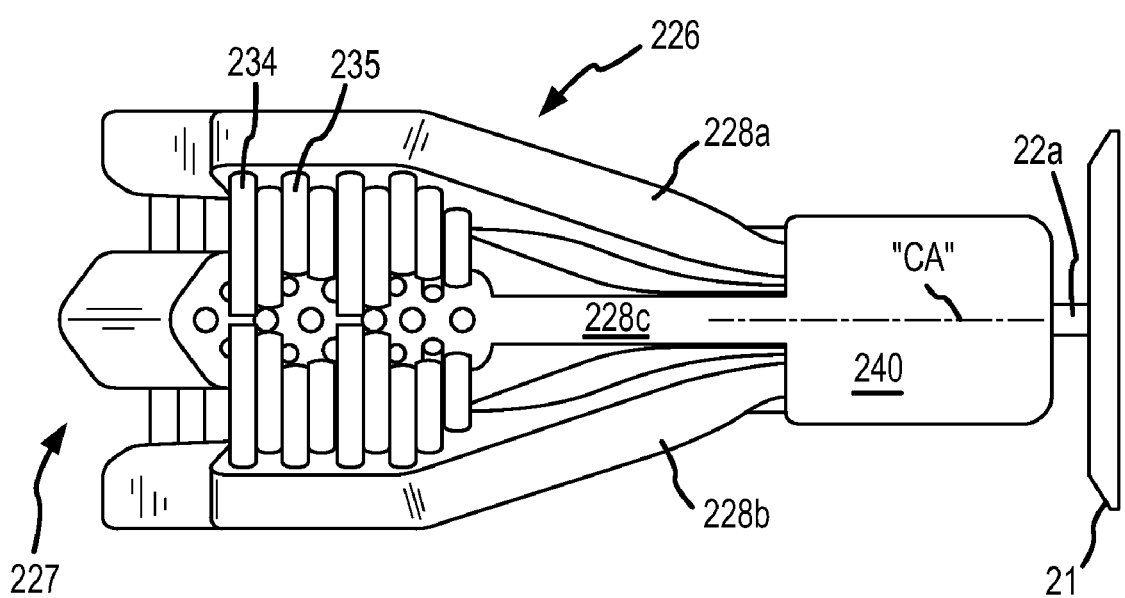
Figure 11A:
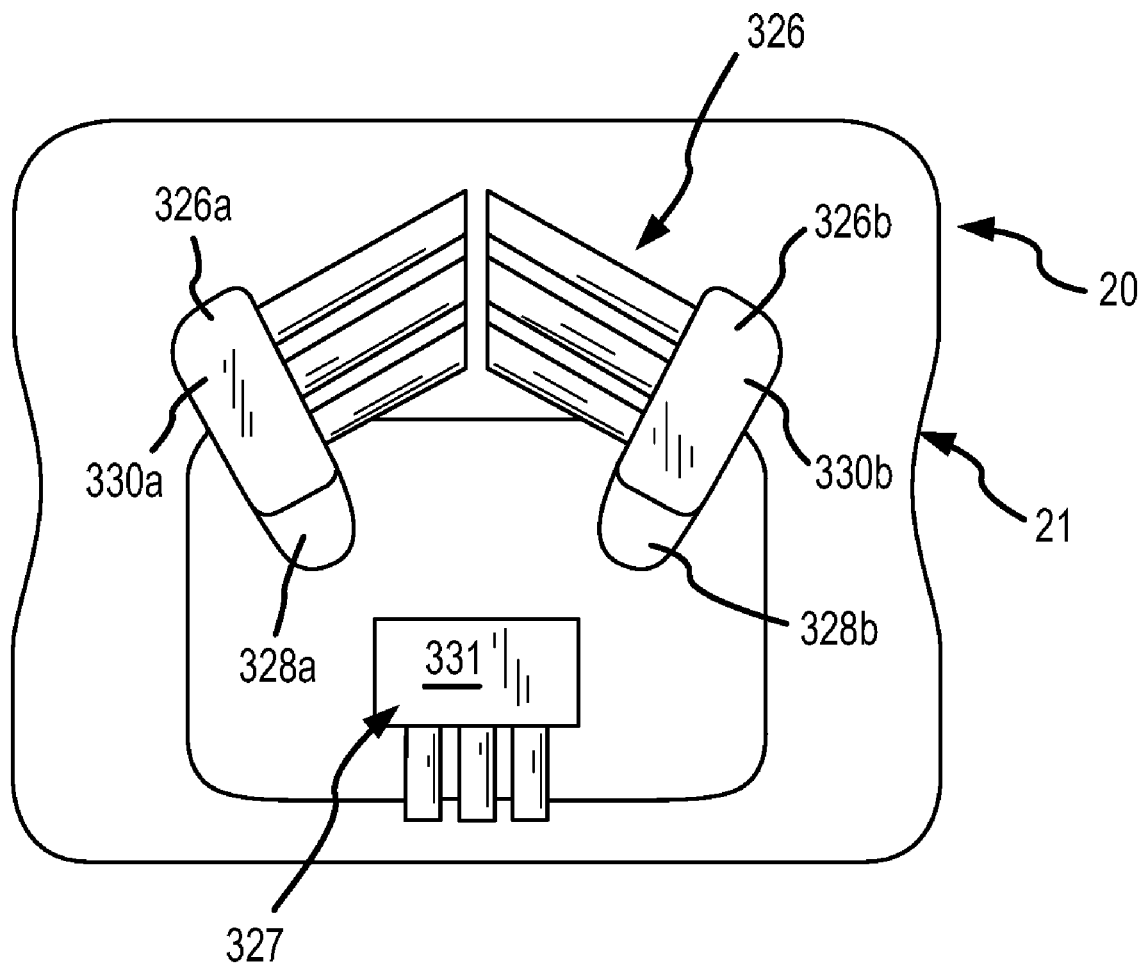

Furthermore, although uneven bristle groups 234, 235 are not necessarily shown in FIGS. 10A-10C, such groups are indicated in FIG. 10D to highlight the optionality hereof as they may, even with tripartite brushes, provide desirable bristle tip coverage of the uneven surfaces of the tooth, as for example on the uneven chewing surface and the uneven side surfaces of FIG. 4. Note also for this or any uneven bristle embodiment (described here or otherwise), the building or manufacture of short and long bristles in one brush can be a more complicated process than many conventional brush processes, by including multiple steps, as in: planting a first set of short bristles, then, trimming those short bristles to the desired point, and then planting the long bristles and finally trimming the long bristles to size.

The respective brush head assembly(ies) 226, 227 can also as described above, be detachably attached to the end of the respective structural brush shafts 22a, 22b. Detachability may be effected through use of depressible button 242 which can release a spring catch (not shown here), and the respective brush head 226 (and/or 227) can then be removed or pulled therefrom. A similar disposition and action may be had with the brushes (if so desired) and the corresponding structural shafts. In some embodiments, the brush head(s) may be installed onto corresponding shafts, until they go on to a point at which the button "snaps" and locks the brush head in relation to the respective structural shaft.

And, yet again as above, the brushes may be reciprocated in short strokes in accordance with ADA recommended Bass technique, brushing with a short/quick back and forth action(s). As such, the control handle 21 may in many implementations be provided with powering means (see e.g., FIGS. 7, 8 and 9) for providing reciprocating longitudinal movement in alternating synchronization of the tripartite brushing head assemblies 226, 227. The upper brush head and lower brush head may be made to move in opposite directions, i.e., when the upper brush head 226 is moving inward, the lower brush head 227 is moving outward. This is desirable in many implementations because when a user bites into the upper and lower brush heads at the same time, the opposing reciprocatable movement can provide a "balance"; e.g., balance of forces, so that the power handle does not tend to move in and out, or otherwise, as a result of the forced movement and/or contact with both the first and second (upper and lower or side to side or other arrangement) brush head simultaneously. The user then may easily hold the device 20 without manual exertion, dexterity or otherwise other than to position the device relative to the mouth.

In general, brush head assemblies could include one or more brush heads. In one further alternative, for example, a singular brush head (not directly shown) could be used. Alternatively or in addition thereto, one or more or an arrangement of brush heads could be disposed for brushing the sides of the teeth and/or the crowns of the teeth. Examples of such arrangements include those brush assemblies 326 and/or 327 shown in FIG. 11. In this way, either a combination of oppositely movable lateral brushes 326a, 326b that can be used on the top teeth (or bottom) while an independent brush 327 may be used on the bottom (or top) teeth. Or one of these brushes 326, 327 or other combinations of brushes could be used independently of the other set of brushes to provide controlled brushing action for top and bottom teeth but on only one side (top, bottom, inside or outside) or on the crowns/chewing surfaces, as desired at a time. Alternation may then be available from a first side to the other side, or top to bottom, etc., or both as desired. As introduced above, positioning the brushes properly may be provided by a guide means which might be provided by the one or more brushes themselves wherein these lock around the teeth through the resiliency of the brush heads and/or arms to correctly position the bristles at the appropriate angles and locations adjacent the teeth and/or gums. Such action may here as well be provided by or receive assistance from a set of resilient arms, e.g., arms 328a, 328b and/or 329 spreading or squeezing a set of one or more brush heads, e.g., brushes 330a or 330b, or 331. Also as before, the opposing brushes can be moved in an alternating brushing action to provide a desirable force balance.

In another, single brush alternative, the single brush may have at least one set of side bristles together with a set of crown bristles, the single brush having a resilient head and/or arm to allow for self-positioning of the respective bristles relative to an oral cavity feature such as a tooth, gum or intersection therebetween. Such a single brush may moreover have two opposing side sets of bristles with or without crown bristles and may have internal head and/or arm resiliency to provide for self-positioning of the respective bristles relative to an oral cavity feature.

From the foregoing, it is readily apparent that new and useful implementations of the present invention have been herein described and illustrated which fulfill numerous desiderata in remarkably unexpected fashions. An assembly such as any of these described herein may be adequate for twin cooperative goals of efficaciously brushing the occlusial and lingual-bucal surfaces, including gaps therebetween, while also simultaneously brushing the aforementioned surfaces and also the underlying teeth and gums thereby providing therapeutical prevention and/or treatment of periodontal problems. It is, of course, understood that such modifications, alterations and adaptations as may readily occur to the artisan confronted with this disclosure are intended within the spirit of this disclosure which is limited only by the scope of the claims appended hereto.

What is claimed is:

1. An oral cleansing device comprising:
 a handle including:
  a housing structure;
  at least one control assembly disposed within the housing structure; and,
  a connection shaft assembly including at least a first shaft and a second shaft stemming from the housing structure; and,
 a first brush assembly adapted to be connected to the first shaft and a second brush assembly adapted to be connected to the second shaft;
 whereby the control assembly is adapted to provide opposing bi-directional linearly straight motion to the first and second brush assemblies.

2. An oral cleansing device according to claim 1 wherein the first and second brush assemblies include respective first and second brushes, the first and second brushes including respective first and second deformably elastic, resilient arms adapted to be connected to the connection configuration, the first and second deformably elastic, resilient arms each respectively having first and second brush heads connected thereto;
 whereby the first and second brushes are operatively disposed such that the first and second brush heads are disposed in generally opposing relationship to each other; and,
 whereby the first and second brush heads each have one or the other or both of respective crown portions and respective side portions.

3. An oral cleansing device according to claim 1 wherein the first and second brush assemblies include respective first and second brush assemblies and the shafts reciprocate in and out and thereby provide for alternating reciprocation of the first and second brush assemblies.

4. An oral cleansing device according to claim 1 wherein the first and second brush assemblies include respective first and second brush assemblies and the shafts reciprocate in opposing directions and thereby provide for alternating reciprocation of the first and second brush assemblies.

5. An oral cleansing device according to claim 1 wherein the first and second brush assemblies include respective first and second brush assemblies and the shafts reciprocate in opposing directions and thereby provide for alternating reciprocation of the first and second brush assemblies, whereby the alternating reciprocation provides balance to the overall device.

6. An oral cleansing device according to claim 1 wherein the first and second brush assemblies include respective first and second brush assemblies and the first and second brush assemblies each include two heads and the shafts reciprocate and thereby provide for alternating reciprocations of the first and second brush assemblies.

7. An oral cleansing device according to claim 1 wherein the first and second brushes are adapted to move linearly straight in short strokes.

8. An oral cleansing device according to claim 1 wherein the first and second brushes are adapted to move linearly straight in short strokes of less than or equal to about 0.25 inches.

9. An oral cleansing device according to claim 1 wherein the first and second brushes are adapted to move linearly straight in slow strokes.

10. An oral cleansing device according to claim 1 wherein the first and second brushes are adapted to move linearly straight in slow strokes of between about 650 and about 850 strokes per minute.

11. An oral cleansing device according to claim 1 wherein the first and second brushes are adapted to move linearly straight in simulation of one or both of the Bass or ADA method.

12. An oral cleansing device according to claim 1 further including a motor, the motor adapted to provide primary power to reciprocate the at least one brush head assembly.

13. An oral cleansing device according to claim 1 whereby the at least one control assembly includes a mechanical system to move the first and second brush assemblies; the mechanical system including:
- a crown gear connected by a gear shaft to a reduction spur gear;
- a double cam gear which communicates in gear meshing relationship with the reduction spur gear; the reduction spur gear being adapted to drive the double cam gear; the double cam gear having respective first and second cams, one each on opposite sides of the double cam gear;
- first and second cam followers each disposed in respective operative contact with the respective first and second cams of the double cam gear, the double-cam gear by contact through the respective first and second cams, being adapted to move the two cam followers in a linear fashion;
- the first and second shafts of the connection shaft assembly each being respectively attached to the respective first and second cam followers, the first and second shafts thus being adapted to move with the respective first and second cam followers and thereby also move the first and second brush assemblies therewith in a linearly straight fashion.

14. An oral cleansing device according to claim 13 further including a motor, the motor adapted to provide primary power to reciprocate the at least one brush head assembly; the motor having a pinion gear in communication with the crown gear; whereby the motor is adapted to directly turn the pinion gear which in turn, turns the crown gear which turns the reduction spur gear to turn the double cam gear.

15. An oral cleansing system comprising:
an oral brush device having:
- a handle including:
  - a housing structure;
  - a pair of linearly movable connection structures stemming from the housing structure; and,
  - at least one control assembly disposed within the housing structure; the at least one control assembly including a power-driven sub-assembly, the power-driven sub-assembly providing movement for the movable connection structure;
- a power assembly; the power assembly being adapted to be connected to the power-driven sub-assembly of the at least one control assembly; and,
- first and second opposing brush assemblies adapted to be detachably attachable to the pair of linearly movable connection structures of the handle;
  - whereby each of the first and second opposing brush assemblies includes at least one brush having at least one resilient, deformably elastic arm adapted to be connected to each of the connection structures, each of the at least one resilient, deformably elastic arms having a respective first and second brush head connected thereto, the respective first and second brush heads each having one or both of a set of side bristles and a set of crown bristles;
  - whereby the first and second brush heads are disposed in opposing relation such that the sets of side bristles are opposing each other; and,
  - whereby the first set of bristles and the second set of bristles are operatively disposed such that the first and second brush heads are adapted to be self-positioning in relation to an oral feature.

* * * * *